(12) United States Patent
Gicquel et al.

(10) Patent No.: US 7,601,350 B2
(45) Date of Patent: Oct. 13, 2009

(54) **ANTIBODIES THAT BIND *M. TUBERCULOSIS* POLYPEPTIDES**

(75) Inventors: Brigitte Gicquel, Paris (FR); Eng Mong Lim, Paris (FR); Denis Portnoi, Paris (FR); Francois-Xavier Berthet, Paris (FR); Juliano Timm, Paris (FR)

(73) Assignee: Institut Pasteur, Paris (FR)

( * ) Notice: Subject to any disclaimer, the term of this patent is extended or adjusted under 35 U.S.C. 154(b) by 1248 days.

(21) Appl. No.: 10/342,232

(22) Filed: Jan. 15, 2003

(65) Prior Publication Data

US 2006/0127959 A1    Jun. 15, 2006

Related U.S. Application Data

(62) Division of application No. 09/579,264, filed on May 26, 2000, now Pat. No. 6,565,855, which is a division of application No. 08/793,701, filed on Jun. 9, 1997, now Pat. No. 6,248,581.

(30) Foreign Application Priority Data

Sep. 2, 1994    (FR) .................................... 94/10585
Aug. 30, 1995    (WO) ...................... PCT/FR95/01133

(51) Int. Cl.
  *A61K 39/00*    (2006.01)
  *A61K 39/395*    (2006.01)
  *A61K 39/40*    (2006.01)

(52) U.S. Cl. ............... 424/139.1; 424/130.1; 424/141.1; 424/150.1; 424/164.1; 424/168.1; 424/248.1; 530/300; 530/350

(58) Field of Classification Search .............. 424/130.1, 424/139.1, 141.1, 150.1, 164.1, 168.1, 248.1; 530/300, 350
See application file for complete search history.

(56) References Cited

U.S. PATENT DOCUMENTS 4,906,742 A * 3/1990 Young et al. ................ 536/23.7

OTHER PUBLICATIONS

Cherayil, B.J. et al. "A 28-kDa protein from *Mycobacterium leprae* is a target of the human antibody response in lepromatous leprosy", Journal of Immunology, vol. 141, pp. 4370-4375, 1988.*

Young, R.A., et al., "Genes for the major protein antigens of the leprosy parasite *Mycobacterium leprae*", Nature, vol. 316, pp. 450-452, Aug. 1, 1985.*

Das Gupta, S. et al., "Cloning and Assessment of Mycobacterial Promoters by Using a Plasmid Shuttle Vector," *J. Bacteriology*, vol. 175, No. 16, pp. 5186-5192 (1993).

Timm, J. et al., "Transcription and Expression Analysis, Using LacZ and phoA Gene Fusions, of *Mycobacterium fortutitum* beta-lactamase Genes Cloned From a Natural Isolate . . . ," *Molecular Microbiology*, vol. 12, No. 3, pp. 491-504 (1994).

Nagai, S. et al., "Isolation and Partial Characterization of Major Protein Antigens In the Culture Fluid of *Mycobacterium tuberculosis*," *Infection and Immunity*, VI. 59, No. 1, pp. 372-382 (1991).

Stover, K. et al., "Protective Immunity Elicited by Recombinant Bacille Calmette-Guerin (BCG) Expressing . . . ," *J. Experimental Medicine*, vol. 178, pp. 197-209 (1993).

Boquet, P. et al., "Use of TnphoA to Detect Genes for Exported Proteins in *Escherichia coli*: Identification . . . ," *J. Bacteriology*, vol. 169, pp. 1663-1669 (1987).

Anderson, P. et al., "Identification of Immunodominant Antigens During Infection with *Mycobacteria tuberculosis*," *Scandinavian J. of Immunology*, vol. 36, pp. 823-831.

Timm, J. et al., *Escherichia coli*-Mycobacteria Shuttle Vectors for Operon and Gene Fusions to IacZ: the pJEM Series, *J. Bacteriology*, vol. 176, pp. 6749-6753 (1994).

Bigi, F. et al., "Characterization of a Novel *Mycobacterium bovis* Secreted Antigen Containing PCLTS Repeats," *Infection and Immunity*, vol. 63, pp. 2581-2586 (1995).

Lim, E., et al., "Identification of *Mycobacterium tuberculosis* DNA Sequences Encoding Exported Proteins . . . ," vol. 177, pp. 59-65 (1994).

Nagai et al., "Isolation and Partial Characterization of Major Protein Antigens in the Culture Fluid of *Mycobacterium tuberculosis*," *Infection of Immunity*, vol. 59, No. 1, pp. 372-382 (1991).

* cited by examiner

*Primary Examiner*—Rodney P. Swartz
(74) *Attorney, Agent, or Firm*—Finnegan, Henderson, Farabow, Garrett & Dunner, L.L.P.

(57) ABSTRACT

Purified antibodies that bind to *M. tuberculosis* ERP protein are disclosed. In one embodiment, a purified antibody, which binds specifically with a polypeptide comprising SEQ ID NO: 39 or SEQ ID NO: 41 is provided. In some embodiments the polypeptide has a theoretical molecular weight of about 28 kDa. In other embodiments the polypeptide has an observed molecular weight of about 36 kDa, as determined by denaturing polyacrylamide gel electrophoresis (SDS-PAGE). The purified antibody may be a monoclonal or a polyclonal antibody. Further embodiments provide antibodies that does not bind specifically with *M. leprae* P28 protein. The antibodies of the invention have many uses including the identification of *M. tuberculosis*.

10 Claims, 18 Drawing Sheets

A. *M. tuberculosis* 19 kDa (pExp410)

Figure 1A:
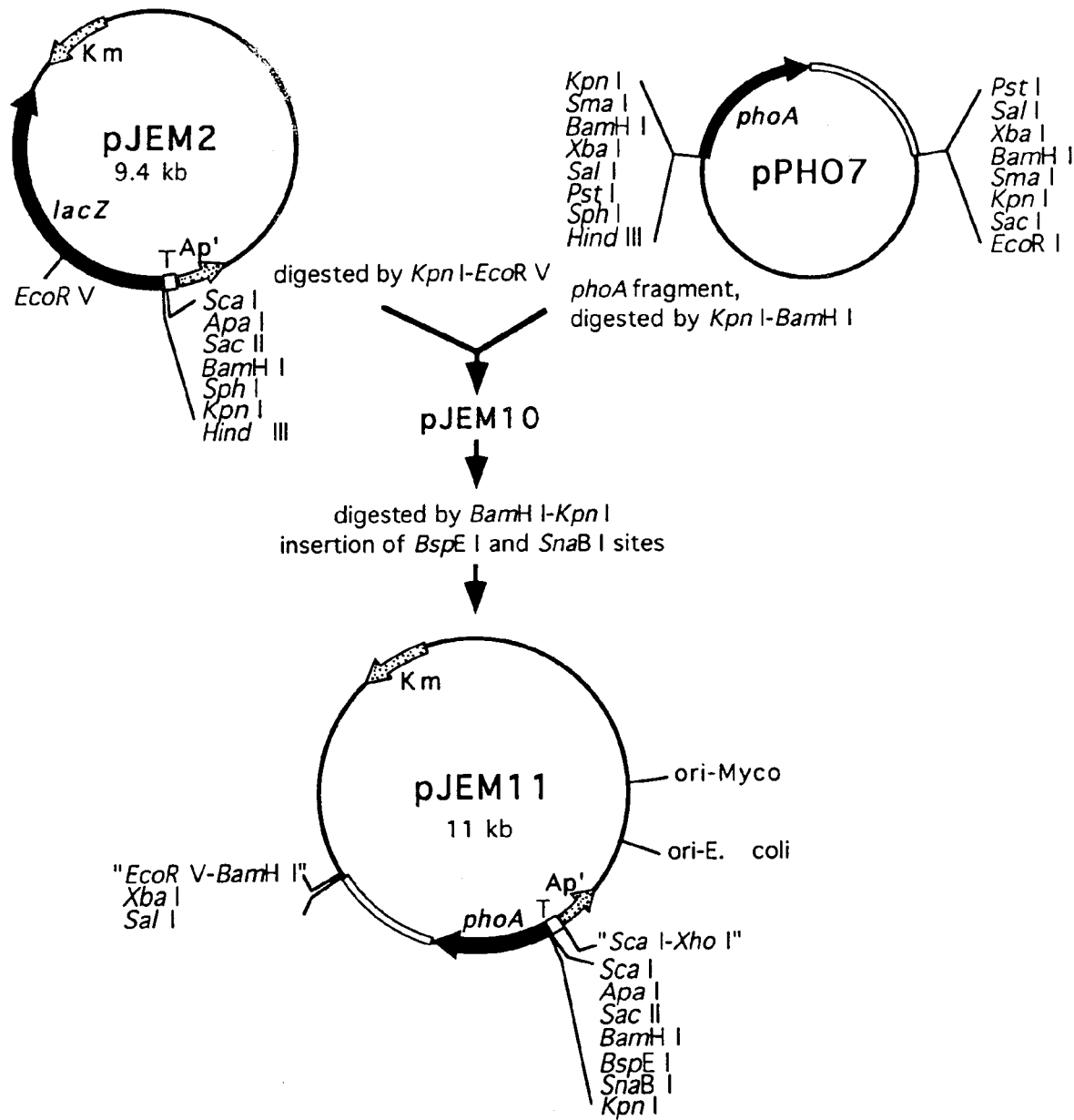

```
          129
          Ser  His  Tyr  Lys  Ile                              SEQ ID NO:19
          AGC  CAC  TAC  AAG  ATC/ C  GG ATA CGT ACG           SEQ ID NO:18
                         Bam H1/Sau 3A    PhoA reading frame
```

B. *M. tuberculosis* 28kDa (pExp53)

```
                                                              10
           Start Pro  Asn  Arg  Ser  Arg  Ser  Lys  Leu  Ser   SEQ ID NO:21
    GTTCC  GTG   CCG  AAC  CGC  AGC  CGC  AGC  AAG  CTC  TCG   SEQ ID NO:20
           :::   :::  :::  :::  ::A  C::  ::A  T::  :::  ::T   SEQ ID NO:22
M. leprae  Start Pro  Asn  Arg  Arg  Arg  Cys  Lys  Leu  Ser   SEQ ID NO:23
                                                    20
           Thr   Ala. Met  Ser  Ala  Val  Ala  Ala  Leu  Ala  Val
           ACA   GCC  ATG  AGC  GCG  GTC  GCC  GCC  CTG  GCA  GTT
           :::   :::  ::A  :::  A::  :::  :::  A::  ::A  :::  A:C
           Thr   Ala  Ile  Ser  Thr  Val  Ala  Thr  Leu  Ala  Ile
                                       70
           Ala | Ser | Pro  ------ Gln  Phe  Gly  Ile             SEQ ID NO:25
           GCA↓ AGT↓ CCT  ------ CAG  TTC  GGG  ATC/ C GG ATA CGT ACG  SEQ ID NO:24
           ::C  :::  ::A  ------ :::  :::       Bam H1/Sau 3A  PhoA reading frame
           Ala  Ser  Pro  ------ Gln  Phe  Gly  Ile
```

C. *M.tuberculosis* (pExp59)

```
                         1
                         Met  Asn  Arg  Ile  Val  Ala   SEQ ID NO:27
        GTCGAGGAGCCACCG  ATG  AAC  CGG  ATC  GTC  GCG   SEQ ID NO:26
          putative RBS Pro  Ala  Ala  Ala  Ser  Val  Val  Val  Gly  Leu
        CCC  GCC  GCC  GCA  AGC  GTG  GTG  GTT  GGT  CTG Leu  Leu  Ala  Pro  Ala ↓Ala  Ile
        TTG  CTG  GCG  CCG  GCC  GCG  ATC/ C  GG ATA CGT ACG
                               Bam H1/Sau 3A   PhoA reading frame
```

D. *M. tuberculosis* (pExp421)

```
           171                                                SEQ ID NO:29
           Trp  Thr  Ala  Glu  Glu  Asn  Arg  His  Gly        SEQ ID NO:28
           TGG  ACC  GCC  GAG  GAG  AAT  CGG  CAC  GGC        SEQ ID NO:30
           :::  ::T  ::G  ::A  :::  :::  A:A  ::T  ::T        SEQ ID NO:31
R. comm    Trp  Thr  Ala  Glu  Glu  Asn  Arg  His  Gly 226
------ Ser  Phe  Gln  Glu  Leu  Ala  Thr  Arg  Ile  Ser  His  SEQ ID NO:33
------ AGT  TTC  CAG  GAA  CTG  GCA  ACC  CGG  ATT  TCG  CAC  SEQ ID NO:32
------ TCA  :::  :::  :::  AG:  :::  :::  TTC  :::  ::T  ::T  SEQ ID NO:34
------ Ser  Phe  Gln  Glu  Arg  Ala  Thr  Phe  Ile  Ser  His  SEQ ID NO:35

Arg  Asn  Thr  ------
       CGC  AAT  ACC  ------
       G:G  ::C  :::  ------
       Gly  Asn  Thr
```

FIG. 4

```
1/1
GTG CCG AAC CGC AGC CGC AGC AAG CTC TCG ACA GCC ATG AGC GTC GCC GCC CTG GCA
M   P   N   R   S   R   S   K   L   S   T   A   M   S   V   A   A   L   A

61/21
GTT GCA AGT CCT TGT GCA TAT TTT CTT GTC TAC GAA TCA ACC GAA ACG GAG CGG CCC
V   A   S   P   C   A   Y   F   L   V   Y   E   S   T   E   T   E   R   P

121/41
GAG CAC CAT GAA TTC AAG CAG GCG GCG GTG TTG ACC GAC CTG CCC GGC GAG CTG ATG TCC
E   H   H   E   F   K   Q   A   A   V   L   T   D   L   P   G   E   L   M   S

181/61
GCG CTA TCG CAG GGG TTG TCC CAG TTC GGG ATC AAC ATA CCG CCG GTG CCC AGC CTG ACC
A   L   S   Q   G   L   S   Q   F   G   I   N   I   P   P   V   P   S   L   T

241/81
GGG AGC GGC GAT GCC AGC ACG GGT CTA ACC GGT CCT GGC CTG ACT AGT CCG GGA TTG ACC
G   S   G   D   A   S   T   G   L   T   G   P   G   L   T   S   P   G   L   T

301/101
AGC CCG GGA TTG ACC AGC ACC AGC CCC GGC CTC GCC ACC GAC CCT CTT ACC CCG GGC CTG ACG
S   P   G   L   T   S   T   S   P   G   L   A   T   D   P   L   T   P   G   L   T

361/121
CCA ACC CTG CCC GGA TCA CTC GCC GCG CCC GGC ACC ACC CTG GCG CCA ACG CCC GGC GTG
P   T   L   P   G   S   L   A   A   P   G   T   T   L   A   P   T   P   G   V

421/141
GGG GCC AAT CCG GCG CTC ACC AAC CCC GCG CTG ACC AGC CCC GGG GCG ACG CCG GGA
G   A   N   P   A   L   T   N   P   A   L   T   S   P   G   A   T   P   G

451/151
```

FIG. 6A-1

```
481/161                                 511/171
TTG ACC AGC CCG ACG GGT TTG GAT CCC GCG CTG GGC GGC GCC AAC GAA ATC CCG ATT ACG
L   T   S   P   T   G   L   D   P   A   L   G   G   A   N   E   I   P   I   T
541/181                                 571/191
ACG CCG GTC GGA TTG GAT CCC GGG GCT GAC GGC ACC TAT CCG ATC CTC GGT GAT CCA ACA
T   P   V   G   L   D   P   G   A   D   G   T   Y   P   I   L   G   D   P   T
601/201                                 631/211
CTG GGG ACC ATA CCG AGC AGC CCC GCC ACC ACC TCC ACC GGC GGC GGC GGT CTC GTC AAC
L   G   T   I   P   S   S   P   A   T   T   S   T   G   G   G   G   L   V   N
661/221                                 691/231
GAC GTG ATG CAG GTG GCC AAC GAG TTG GGC GCC AGT CAG GCT ATC GAC CTG CTA AAA GGT
D   V   M   Q   V   A   N   E   L   G   A   S   Q   A   I   D   L   L   K   G
721/241                                 751/251
GTG CTA ATG CCG TCG ATC ATG CAG GCC GTC CAG AAT GGC GGC CGC GTC GCG CCG GCA GCC
V   L   M   P   S   I   M   Q   A   V   Q   N   G   G   A   V   A   P   A   A
781/261                                 811/271
AGC CCG CCG GTC CCG CCC ATC CCC GCG GCC GCG GCG GTG CCA CCG ACG GAC CCA ATC ACC
S   P   P   V   P   P   I   P   A   A   A   A   V   P   P   T   D   P   I   T
841/281
GTG CCG GTC GCC TAA  SEQ ID NO: 38
V   P   V   A   *    SEQ ID NO: 39
```

Nucleotide sequence and deduced amino acid sequence of the potential product of the *M. tuberculosis* IRSA gene

FIG. 6A-2

```
1/1
GTG CCG AAC CGA CGC CGC AAG CTC TCG ACA GCC ATG AGC GCG GTC GCC CTG GCA
 M   P   N   R   R   R   K   L   S   T   A   M   S   A   V   A   L   A
                              31/11
61/21
GTT GCA AGT CCT TGT GCA TAT TTT CTT GTC GCG GCG GTG TAC GAA ACC GAG CGG CCC
 V   A   S   P   C   A   Y   F   L   V   A   A   V   Y   E   T   E   R   P
                              91/31
121/41
GAG CAC CAT GAA TTC AAG CAG GGG TTG TCC CAG TTC GAC CTG CCC GGC GAG CTG ATG TCC
 E   H   H   E   F   K   Q   G   L   S   Q   F   D   L   P   G   E   L   M   S
                              151/51
181/61
GCG CTA TCG CAG GGG TTG ACC AGC ACG GGT CTA ACC GTG CCC GTG CCC AGC CTG ACC
 A   L   S   Q   G   L   T   S   T   G   L   T   V   P   V   P   S   L   T
                              211/71
241/81
GGG AGC GGC GAT GCC AGC CCG GGT CCT GGC CTG ACT AGT CCG GGA TTG ACC
 G   S   G   D   A   S   P   G   P   G   L   T   S   P   G   L   T
                              271/91
301/101
AGC CCG GGA TTG ACC AGC CCT GCC GAC CCT GCC CTT ACC AGT CCG GGC CTG ACG
 S   P   G   L   T   S   P   A   D   P   A   L   T   S   P   G   L   T
                              331/111
361/121
CCA ACC CTG CCC GGA TCA CTC GCC GCG CCC ACC CTG GCG ACC CCG GGC GTG
 P   T   L   P   G   S   L   A   A   P   T   L   A   T   P   G   V
                              391/131
421/141
GGG GCC AAT CCG GCG CTC ACC AAC CCC GCG CTG ACC AGC CCG ACG CCG GGA
 G   A   N   P   A   L   T   N   P   A   L   T   S   P   T   P   G
                              451/151

FIG. 6B-1
```

```
481/161
TTG ACC AGC CCG ACG GGT TTG GAT CCC GCG CTG GGC GCC AAC GAA ATC CCG ATT ACG
 L   T   S   P   T   G   L   D   P   A   L   G   A   N   E   I   P   I   T
541/181                                                       511/171
ACG CCG GTC GGA TTG GAT CCC GGG GCT GAC ACC TAT CCG ATC CTC GGT GAT CCA ACA
 T   P   V   G   L   D   P   G   A   D   T   Y   P   I   L   G   D   P   T
601/201                                   571/191
CTG GGG ACC ATA CCG AGC AGC CCC GCC ACC TCC ACC GGC GGC GGT CTC GTC AAC
 L   G   T   I   P   S   S   P   A   T   S   T   G   G   G   L   V   N
661/221                               631/211
GAC GTG ATG CAG GTG GCC AAC GAG TTG GGC GCC AGT CAG GCT ATC GAC CTG CTA AAA GGT
 D   V   M   Q   V   A   N   E   L   G   A   S   Q   A   I   D   L   L   K   G
721/241                           691/231
GTG CTA ATG CCG TCG ATC ATG CAG GCC GTC CAG AAT GGC CGC GTC GCG CCG GCA GCC
 V   L   M   P   S   I   M   Q   A   V   Q   N   G   R   V   A   P   A   A
781/261                       751/251
AGC CCG CCG GTC CCG CCC ATC CCC ATC CCG GCG GCG GTG CCA CCG ACG GAC CCA ATC ACC
 S   P   P   V   P   P   I   P   I   P   A   A   V   P   P   T   D   P   I   T
841/281                   811/271
GTG CCG GTC GCC TAA   SEQ ID NO: 40
 V   P   V   A   *    SEQ ID NO: 41
```

Nucleotide sequence and deduced amino acid sequence of the potential product of the *M.tuberculosis* IRSA gene

FIG. 6B-2

Nucleotide sequences flanking the *M. tuberculosis* IRSA gene

A - Upstream nucleotide sequence:

5'-CGGCTTCGGAATAGGCATTGCCCCCGATGTGCGGGCGCCGCTCGAGGACGAGCACGCGCTTGTC
GAGTTGGGTGGACACGCGCTCGGCAATCGTCAGGCCGAAGAATCCTGAGCCGACGACGAAAAGGTCA
AAACGAGCGGTCATCGGTTGCATAGGGTAACCGACCTTGCTGGCAAAACCCGATTTGGCAGCTCGTG
GCGGTCATGGCCCGAACGGGTTTCACCGCAGGTGCGCATGGCCGACCAGTGTGGTTGGCCGGAGGTC
GTTTGGTCGCGATTGCCTCACGATTCGATATAACCACTCTAGTCACATCAACCACACTCGTACCATC
GAGCGTGTGGGTTCATGCCATGCACTCGCGACCGCGGGAGCCGGCGAACCCGGCGCCACACATAATC
CAGATTGAGGAGACTTCC GTG CCG AAC 3' SEQ ID NO:36
      SD          Met Pro Asn ... géne IRSA

SD           "Shine-Delgarno" putative ribosome binding site

Met          Initiator methionine of the IRSA gene

B - Downstream nucleotide sequence:

Pro Val Stop
IRSA gene .5'- GTC GCC TAA GCCCCGGGTCGGCCGAAAACGCACCCGCGGCCAAGGCG
TCGGTCATTGCTTCGGCCCGTGCACAATTATTCGCCTAAGGGTCGGCTAGGTGTTCTCGAGAGTTTT
ATCGCACCGATTCCGTGTCGTCTCATTAATACCAATAGAAAACACACGTAACATCAGCTGGTGCCGT
CCCGCACCCGCGCGCCGACGACGCTGCTCACCGCGATGGCAGCGACCGTCGTCATCGTCGCGTGGAT
AGCGAATCGTCCACCCGCCAGCTCCCAT 3' SEQ ID NO:37

FIG. 7

Bacterial iron-regulating genes (IRG's)

```
                         -35                              -10
  iucA P1      CATTTCTCATT GATA ATGAgAATCATTATt      GACA  SEQ ID NO:42 sltA         AGCCTCTCTTT GAat ATGATtATCATTtTC      ATTA  SEQ ID NO:43
  fhuA         TATTATCTTAT ctTt ATaATAATCATTcTC      GTTT  SEQ ID NO:44
  fepA         TATATTAGTAA tATt ATGATAActATTtgC      ATTT  SEQ ID NO:45
  fur          CGTGGCAATTC tATA ATGATAcgCATTATC      TCAA  SEQ ID NO:46
  fhuE         TGAATGCGTAT atTt cTcATttgCATTtaC      AAAC  SEQ ID NO:47
  tonB         TTATTGAATAT GATt gctATttgCATTtaa      ATCG  SEQ ID NO:48
  tox          TAATTAGGATA GcTt taccTAAtTATTtTa      TAGC  SEQ ID NO:49
                              --------> <--------
  consensus               GATA ATGATAATCATTATC             SEQ ID NO:50
  M. Leprae 28 kD   CAATTACCTCAcGATtcAatATAAcCAcTcTg  GTCA SEQ ID NO:51
                                    _____
                                       -35
```

28 kDA Mycobacterium leprae gene

5' GATTCAATATAACCACTCTG 3'    SEQ ID NO:52
         *                 *

5' GATTCGATATAACCACTCTA 3'    SEQ ID NO:53

Clone 5-3 of Mycobacterium tuberculosis

FIG. 8

```
M. tuberculosis  1    GTGCCGAACCGCAGCCGCAGCAAGCTCTCGACAGCCATGAGCGCGGTCGC   50  SEQ ID NO:54
M. Leprae        1    GTGCCGAACCGACGCCGATGCAAGCTTTCGACAGCCATAAGCACGGTCGC   50  SEQ ID NO:55

51   CGCCCTGGCAGTTGCAAGTCCTTGTGCATATTTTCTTGTCTACGAATCAA   100
                 51   CACCCTAGCAATCGCCAGTCCATGCGCATATTTCCTTGTTTACGAACCGA   100

101  CCGAAACGACCGAGC...GGCCCGAGCACCATGAATTCAAGCAGGCGGCG   147
                 101  CCGCGAGCGCCAAACCCGCGGCCAAACACTATGAATTCAAACAAGCAGCA   150

148  GTGTTGACCGACCTGCCCGGCGAGCTGATGTCCGCGCTATCGCAGGGGTT   197
                 151  TCGATAGCCGACCTGCCCGGAGAAGTGCTGGACGCGATCTCGCAGGGACT   200

198  GTCCCAGTTCGGGATCAACATACCGCCGGTGCCCAGCCTGACCGGGAGCG   247
                 201  GTCGCAGTTCGGCATCAACCTACCGCCGGTGCCTTCGCTAACTGGCACCG   250

248  GCGATGCCAGCACGGGTCTAACCGGTCCTGGCCTGACTAGTCCGGGATTG   297
                 251  ATGAT...............CCAGGTAATGGCCTGAGAACTCCCGGTTTG   285

298  ACCAGCCCGGGATTGACCAGCCCGGGCCTCACCGACCCTGCCCTTACCAG   347
                 286  ACCAGCCCCGATCTGACAAATCAGGAGCTAGGGACACCTGTGCTCACCGC   335

348  TCCGGGCCTGACGCCAACCCTGCCCGGATCACTCGCCGCGCCCGGCACCA   397
                 336  GCCGGGCACGGGACTGACACCACCTGTGACAGGCAGCCCGATATGTACCG   385

398  CCCTGGCGCCAACGCCCGGCGTGGGGGCCAATCCGGCGCTCACCAACCCC   447
                 386  CAC...............................................   388
```

ALIGNMENT OF NUCLEOTIDE SEQUENCES

FIG. 10A(1)

| | | |
|---|---|---|
| M. Tuberculosis | 448 GCGCTGACCAGCCCGACCGGGGGCGGATTGACCAGCCCGACGGG | 497 |
| M. Leprae | 389 ........................................CGGA | 392 |
| | 498 TTTGGATCCCGCGCTGGGGCGGCCAACGAA

```
M. Tuberculosis    1   MPNRRRRKLSTAMSAVAALAVASPCAYFLVYESTETTER.PEHHEFKQAA      49  SEQ ID NO:57
                       ||||..:||||:.||..||:||||||||||||:|||||. ..:.:||||||
M. Leprae          1   MPNRRRCKLSTAISTVATLAIASPCAYFLVYEPTASAKPAAKHYEFKQAA      50  SEQ ID NO:58

50   VLTDLPGELMSALSQGLSQFGINIPPVPSLTGSGDASTGLTGPGLTSPGL       99
                       :.||||:::.|:|||||:||||||||||||||.:|::.|| .||||||:|
                  51   SIADLPGEVLDAISQGLSQFGINLPPVPSLTGTDDPGNGLRTPGLTSPDL      100

100   TSPGLTSPGLTDPALTSPGLTPTLPGSLAAPGTTLAPTPGVGANPALTNP      149
                       |..:.|.||:|.|:   .||||.:.||
                 101   TNQELGTPVLTAPG...TGLTPPVTGS......................      124

150   ALTSPTCATPGLTSPTGLDPALGGANEIPITTPVGLDPGADGTYPILGDP      199
                                 .:.:|:   .:.|||||:||||||||:|||||||:||||||
                 125   ..........PICTAPDLNLGGTCPSEVPITTPISLDPGTDGTYPILGDP      164

200   .TLGTIPSSPATTSTGGGGLVNDVMQVANELGASQAIDLLKGVLMPSIMQ      248
                       |||     :....:|||::.|||:|.:|||:|.:||::||.:||
                 165   STLG....GTSPISTSSGELVNDLLKVANQLGASQVMDLIKGVVMPAVMQ      210

249   AVQNGGAVAPAASPPVPPIPAAAAVPPTDPITVPVA                284
                       :||||.||..||...|.|.:|..:||.:
                 211   GVQNGN.VAGDLSGSVTP.AAISLIPVT........                236

ALIGNMENT OF AMINO ACID SEQUENCES

FIG. 10B
```

ANTIBODIES THAT BIND *M. TUBERCULOSIS* POLYPEPTIDES

CROSS REFERENCE TO RELATED APPLICATIONS

This application is a division of application Ser. No. 09/579,264, filed May 26, 2000, now U.S. Pat. No. 6,565,855, which is a division of application Ser. No. 08/793,701, filed Jun. 9, 1997, now U.S. Pat. No. 6,248,581, and claims the benefit of international application Ser. No. PCT/FR95/01133, filed Aug. 30, 1995, and French application No. FR 94/10585, filed Sep. 2, 1994, all of which are incorporated herein by reference.

The Mycobacterium genus includes major human pathogens such as *M. leprae* and *M. tuberculosis*, the agents responsible for leprosy and tuberculosis, which remain serious public health problems world-wide.

*M. bovis* and *M. tuberculosis*, the causative agents of tuberculosis, are intracellular faculatative bacteria. Despite the major health problems linked to these pathogenic organisms, little is known about their exported and/or secreted proteins. In SDS-PAGE analyses of *M. tuberculosis* culture filtrate show at least 30 secreted proteins (1, 19, 38). Some of them have been characterized, their genes cloned and sequenced (7, 35, 37). Others, although they are immunodominant antigens of major importance for inducing protective immunity (2, 21), have not been completely identified. In addition, it is probable that a great number of exported proteins remain attached to the cell membrane and, consequently, are not present in culture supernatants. It has been shown that proteins located at the outer surface of various pathogenic bacteria, such as the 103 kDa *Yersina pseudotuberculosis* invasin (14) or the 80 kDa *Listeria monocytogenes* internalin (10) play an important role in interactions with the host cells and, consequently, in pathogenicity as in the induction of protective responses. Thus, a membrane-bound protein could be important for *M. tuberculosis* infection as well as for the induction of a protective response against this infection. These proteins could certainly be of interest for the preparation of vaccines.

The BCG (Bacille Calmette Guérin), an avirulent strain derived from *M. bovis*, has been widely used as vaccine against tuberculosis. It is also a very important vector for the construction of live recombinant vaccines, particularly because of its high immunogenicity. Consequently, the study of the molecular biology of mycobacteria is currently of great interest.

SUMMARY AND DETAILED DESCRIPTION OF THE INVENTION

The development of new vaccines against pathogenic mycobacteria, or the improvement of available vaccines required the development of specific tools which make it possible to isolate or obtain immunogenic polypeptide sequences.

The inventors have defined and produced, for this purpose, new vectors allowing the screening of mycobacteria DNA sequences in order to identify, among these sequences, nucleic acids encoding proteins of interest.

Vectors have been defined for evaluating the efficacy of sequences for regulation of expression in mycobacteria.

The invention also relates to new mycobacteria polypeptides which may have been isolated by means of the preceding vectors and capable of entering into the production of compositions for the detection of a mycobacteria infection, or for protection against an infection due to mycobacteria.

The subject of the invention is therefore a recombinant screening and/or cloning and/or expression vector, characterized in that it replicates in mycobacteria, in that it contains 1) a replicon which is functional in mycobacteria;
2) a selectable marker;
3) a reporter cassette comprising
   a) a multiple cloning site (polylinker),
   b) a transcription terminator which is active in mycobacteria, upstream of the polylinker, and
   c) a coding nucleotide sequence derived from a gene encoding a marker for expression and/or export and/or secretion of protein, said nucleotide sequence lacking its initiation codon and its regulatory sequences.

The marker for export and/or section is a nucleotide sequence whose expression followed by export and/or secretion depends on regulatory elements which control its expression.

"Sequence or elements for regulation of expression" is understood to mean a promoter sequence for transcription, a sequence comprising the ribosome-binding site (RBS), the sequence responsible for export and/or secretion such as th sequence termed signal sequence.

A first advantageous marker for export and/or expression is a coding sequence derviced from the PhoA gene. Where appropriate, it is truncated such that the alkaline phosphatase activity is, nevertheless, capable of being restored when the truncated coding sequence is placed under the control of a promoter and of appropriate regulatory elements.

Other markers for exposure and/or export and/or secretion may be used. There may be mentioned by way of examples a sequence of the gene for β-agarase or for nuclease of a staphylococcus or for β-lactamase of a mycobacterium.

The transcription terminator should be functional in mycobacteria. An advantageous terminator is, in this regard, the T4 coliphage terminator (tT4). Other terminators appropriate for carrying out the invention may be isolated using the technique presented in the examples, for example by means of the vector pJN3.

A vector which is particularly preferred for carrying out the invention is the plasmid pJEM11 deposited at CNCM (Collection Nationale de Cultures de Microorganismes in Paris—France) under the No. I-1375, on 3 Nov. 1993.

For the selection or the identification of mycobacteria nucleic acid sequences encoding products capable of being incorporated into immunogenic or antigenic compositions for the detection of a mycobacteria infection, the vector of the invention will comprise, in one of the polylinker sites, a nucleotide sequence from a mycobacterium in which the presence of regulatory sequences is being sought which are associated with all or part of a gene of interest making it possible, when the vector carrying these sequences (recombinant vector), is integrated or replicates in a mycobacterium-type cellular host, to obtain the exposure at the level of the cell wall or membrane of the host, and/or export and/or secretion of the product of expression of the abovementioned nucleotide sequence.

The mycobacteria sequence in question may be any sequence for which attempts are made to detect if it contains elements for regulation of expression associated with all or part of a gene of interest and capable of allowing or promoting exposure at the level of the cell membrane of a host in which it might be expressed, and/or export and/or secretion of a product of expression of a given coding sequence and, by way of test, of the marker for export and/or secretion.

Preferably, this sequence is obtained by enzymatic digestion of the genomic DNA or of the DNA complementary to an RNA of a mycobacterium and preferably of a pathogenic mycobacterium.

According to a first embodiment of the invention, the enzymatic digestion of the genomic DNA or of the complementary DNA is carried out using *M. tuberculosis.*

Preferably, this DNA is digested with an enzyme such as sau3A.

Other digestive enzymes such as ScaI, ApaI, ScaII, KpnI or alternatively exonucleases or polymerases, may naturally be used, as long as they allow fragments to be obtained whose ends may be inserted into one of the cloning sites of the polylinker of the vector according to the invention.

Where appropriate, digestions with different enzymes will be carried out simultaneously.

Preferred recombinant vectors for carrying out the invention are chosen among the following recombinant vectors deposited at CNCM on 8 Aug. 1994:
pExp53 deopsited at CNCM under the No. I-1464
pExp59 deposited at CNCM under the No. I-1465
pExp410 deposited at CNCM under the No. I-1466
pEXp421 deposited at CNCM under the No. I-1467.

The vectors of the invention may also be used to determine the presence of sequences of interest, according to what was stated above, in mycobacteria such as *M. africanum, M. bovis, M. avium* or *M. leprae* whose DNA or cDNA will have been treated with determined enzymes.

The subject of the invention is also a process for screening nucleotide sequences derived from mycobacteria, to determine the presence, in these sequences, of regulatory elements controlling the expression, in a cellular host, of nucleic acid sequences containing them, and/or exposure at the surface of the cellular host and/or export and/or secretion of the polypeptide sequences resulting from the expression of the abovementioned nucleotide sequences, characterized in that it comprises the following steps:
a) digestion of mycobacteria DNA sequences with at least one determined enzyme and recovery of the digests obtained.
b) insertion of the digests into a cloning site, compatible with the enzyme of step a), of the polylinker of a vector above,
c) if necessary, amplification of the digest contained in the vector, for example by replication of the latter after insertion of the vector thus modified into a determined cell, for example *E. coli,*
d) transformation of cellular hosts by the vector amplified in step c), or in the absence of amplification, by the vector of step b),
e) culture of the transformed cellular hosts in a medium allowing visualization of the marker for export and/or secretion which is contained in the vector,
f) detection of the cellular hosts which are positive for the expression of the marker for exposure and/or export and/or secretion (positive colonies),
g) isolation of the DNA of the positive colonies and insertion of this DNA into a cell which is identical to that of step c),
h) selection of the inserts contained in the vector, which allow clones to be obtained which are positive for the marker for export and/or secretion,
i) isolation and characterization of the fragments of DNA of mycobacteria which are contained in these inserts.

The carrying out of this process allows the construction of DNA libraries containing sequences capable of being exported and/or secreted, when they are produced in recombinant mycobacteria.

Step i) of the process may comprise a step for sequencing the inserts selected.

Preferably, the vector used is the plasmid pJEM11 (CNCM I-1375) and the digestion is carried out by means of the enzyme sau3A.

According to a preferred embodiment of the invention, the screening process is characterized in that the mycobacteria sequences are derived from a pathogenic mycobacteria, for example from *M. tuberculosis, M. bovis, M. avium, M. africanum* or *M. leprae.*

The subject of the invention is also the nucleotide sequences of mycobacteria selected after carrying out the process described above.

According to a specific embodiment of the invention, advantageous sequences are for example the mycobacteria DNA fragments contained in the vectors pIPX412 (CNM I-1463 deposited on Aug. 8, 1994), pExp53, pExp59, pExp410 or pExp421.

When the coding sequence derived from the marker gene for export and/or secretion is a sequence derived from the PhoA gene, the export and/or secretion of the product of the PhoA gene, truncated where appropriate, is obtained only when this sequence is inserted in phase with the sequence placed upstream, which contains the elements controlling the expression and/or export and/or secretion which are derived from a mycobacteria sequence.

The subject of the invention is also recombinant mycobacteria containing a recombinant vector described above. A preferred mycobacterium is a mycobacterium of the *M. smegmatis* type.

*M. smegmatis* makes it possible, advantageously, to test the efficiency of mycobacteria sequences for controlling the expression and/or export and/or secretion of a given sequence, for example of a sequence encoding a marker such as alkaline phosphatase.

Another advantageous mycobacterium is a mycobacterium of the *M. bovis* type, for example the BCG strain currently used for vaccination against tuberculosis.

A subject of the invention is, moreover, a recombinant mycobacterium, characterized in that it contains a recombinant vector defined above.

The invention also relates to a nucleotide sequence derived from a gene encoding an exported *M. tuberculosis* protein, characterized in that it is chosen from the following sequences:
a sequence IA corresponding to the chain of nucleotides described in FIG. 6A, or a sequence IB corresponding to the chain of nucleotides described in FIG. 6B, or hybridizing under stringent conditions with these chains,
a sequence II comprising the chain of nucleotides IA or IB and encoding an *M. tuberculosis* P28 protein having a theoretical molecular weight of about 28 kDa and an observed molecular weight of 36 kDa, determined by denaturing acrylamide gel electrophoresis (SDS-PAGE)
a sequence III contained in the sequence IA or IB and encoding a polypeptide recognized by antibodies directed against the *M. tuberculosis* P28 protein,
a sequence IV comprising the regulatory sequences of the gene comprising the coding sequence IA or IB,
a sequence V corresponding to the chain between nucleotides 1 and 72 of the sequence IA or IB and corresponding to the signal sequence.
a sequence VI corresponding to the chain between nucleotides 62 to 687 of the sequence IA or IB,
a sequence VII corresponding to the chain between nucleotides 688 and 855 of the sequence IA or IB.

Also entering within the framework of the invention is an *M. tuberculosis* polypeptide characterized in that it corresponds to the amino acid chain VIIIA or to the chain VIIIB represented in FIGS. 6A and 6B respectively or in that it comprises one of these chains.

A preferred polypeptide is characterized in that it has a theoretical molecular weight of about 28 kDa determined according to the technique described in the examples.

The *M. tuberculosis* p28 protein has been characterized by its capacity to be exported and therefore potentially located across the bacterial plasma membrane or the cell wall. Furthermore, as shown in the sequences presented in FIG. 6, some peptide units of the sequence are repeated. For these reasons, the *M. tuberculosis* p28 protein is now most often designated as ERP protein and the gene containing the coding sequence for this protein is called either irsa gene or erp gene.

The theoretical molecular weight of the ERP protein, evaluated at 28 kDa, corresponds to an experimentally observed molecular weight of about 26 kDa (electrophoretic migration on a denaturing polyacrylamide gel (DOS-PAGE)).

Another advantageous polypeptide within the framework of the invention comprises part of the amino acid chain VIII or VIIIB previously described and immunologically reacts with antibodies directed against the *M. tuberculosis* p28 protein.

Preferably, such a polypeptide is, in addition, characterized in that it does not immunologically react with the *M. leprae* p28 protein.

Particularly advantageous amino acid sequences within the framework of the invention are the sequences comprising one of the following chains or corresponding to one of these chains in one or more copies: PGLTS (SEQ ID NO: 1), PGLTD (SEQ ID NO: 2), PGLTP (SEQ ID NO: 3), PALTN (SEQ ID NO: 4), PALTS (SEQ ID NO: 5), PALGG (SEQ ID NO: 6), PTGAT (SEQ ID NO: 7), PTGLD (SEQ ID NO: 8), PVGLD (SEQ ID NO: 9).

Other advantageous sequences are, for example, the signal sequence between the positions of nucleotides 1 and 72 of the sequence of FIG. 6A or 6B or alternatively the sequence between nucleotides 688 and 855 which is capable of behaving like a transmembrane sequence.

These polypeptide sequences may be expressed in the form of recombinant polypeptides. In these recombinant polypeptides, they may be replaced in part especially as regards the sequences of 5 amino acids previously described, by sequences of interest obtained from mycobacteria or other pathogenic organisms, it being possible for this replacement to lead to the inclusion, inside the recombinant polypeptides, of the epitopes or the antigenic determinants of a pathogenic organism or of a protein of interest against which it might be sought to obtain antibodies.

Thus, the polypeptides of the invention, while optionally exhibiting themselves the antigenic or even immunogenic properties, may be used as advantageous carrier molecules for preparing, where appropriate, vaccines having varying properties.

The subject of the invention is also monoclonal antibodies or polyclonal sera directed against a polypeptide as defined above.

As regards monoclonal antibodies, they are preferably directed specifically against a polypeptide of the invention and do not recognize, for example, the *M. leprae* p28 protein.

The subject of the invention is also a composition for the in vitro detection of an *M. tuberculosis* infection, characterized in that it comprises a polypeptide defined above, which is capable of immunologically reacting with antibodies formed in a patient infected with *M. tuberculosis*.

Another composition for the in vitro detection of an *M. tuberculosis* infection is characterized by a nucleotide sequence containing at least 9 nucleotides, which is derived from a sequence defined above, or a nucleotide sequence containing at least 9 nucleotides and hybridizing, under stringent conditions, with *M. tuberculosis* DNA and not hybridizing, under the same conditions, with *M. leprae* DNA, this sequence being a DNA or RNA sequence, which is labeled where appropriate.

The subject of the invention is also a prokaryotic or eukaryotic cellular host, characterized in that it is transformed by a nucleotide sequence as described in the preceding pages, under conditions allowing the expression of this sequence and/or its exposure at the level of the membrane of the cellular host and/or its export and/or its secretion from the abovementioned membrane.

Preferably, the cellular hosts are mycobacteria such as *M. smegmatis* or *M. bovis* BCG.

Other cellular hosts are for example *E. coli*, CHO, BHK, Spf9/Baculovirus cells, yeasts such as *Saccharomyces cerevisiae*, vaccinia virus.

The subject of the invention is also an immunogenic composition comprising a polypeptide as presented above or a cellular host as defined above.

The invention relates, moreover, to a vector for the screening and/or cloning and/or expression of nucleotide sequences which are functional in myco-bacteria, and which is derived from a vector described above and characterized in that the coding sequence derived from a gene encoding a marker for export and/or secretion is replaced by a reporter gene or a reporter sequence.

Preferably, the reporter sequence or gene lacks its regulatory sequences, in particular its ribosome binding sequences and/or its sequences which allow the export and/or secretion of the marker produced when the vector is incorporated into a recombinant cellular host.

Preferably, the reporter sequence or gene contains the sequence encoding the lacZ gene or a part of this sequence which is sufficient for the polypeptide to exhibit a β-galactosidase activity.

A preferred vector of the invention is characterized in that it comprises at one of the cloning sites of the polylinker, a chain of nucleotides comprising a promoter and, where appropriate, regulatory sequences, for example for anchorage at the surface, the export or even the secretion of a polypeptide which might be produced under the control of the promoter, for which it is desired to evaluate the capacity to promote or regulate the expression of a reporter nucleotide sequence in mycobacteria.

Figures 12A, 12B:
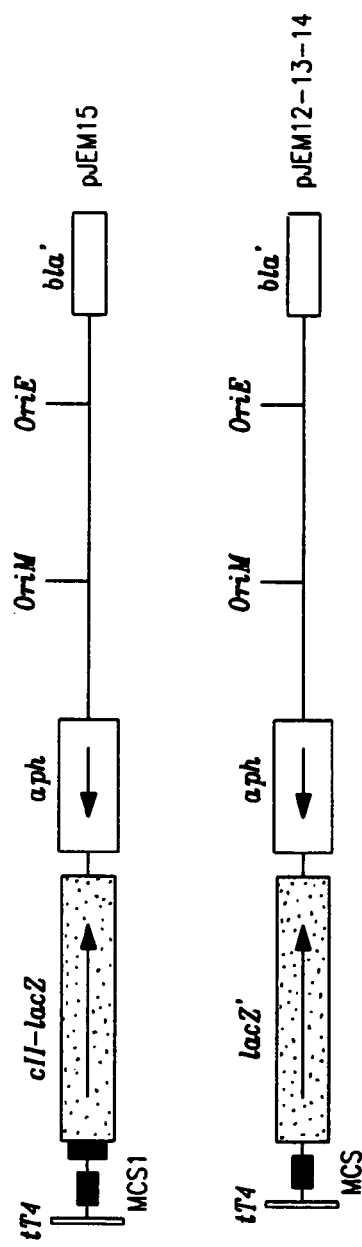

Preferred vectors are plasmids chosen from the plasmids pJEM12, pJEM13, pJEM14, or pJEM15 as represented in FIG. 12.

Such a vector may be used to evaluate the value of sequences for regulation of expression or of promoters, for example, the pAN, pblaF*, PSU13, pgroES/ELI sequences.

The invention also comprises a process for determining the activity of a sequence containing at one of the cloning sites of the polylinker a chain of nucleotides comprising a promoter and, where appropriate, regulatory sequences, for example for the exposure, export or even secretion of a polypeptide which might be produced under the control of the promoter in mycobacteria, characterized in that it comprises the steps of:

transforming a mycobacterium strain, for example *M. smegmatis* or *M. tuberculosis*, with a vector described above, detecting the activity normally associated with the presence of the reporter gene or of the reporter sequence.

Other characteristics and advantages of the invention appear on reading the examples which follow as well as in the figures.

LEGEND TO THE FIGURES

FIG. 1

Construction of pJEM11.

See Materials and Methods. pJEM11 has replication origins (ori) of *E. coli* and mycobacteria. It is therefore a shuttle plasmid. The selectable marker is the kanamycin (Km) resistance gene. The truncated PhoA gene of pPH07 (22) lacks a promoter, a start codon and a signal sequence; thus the expression and export of PhoA depend on the translational fusion with the amino-terminal ends of other proteins. The transcriptional terminator (T) of the omega cassette avoids transcription by "read-through" using plasmid sequences.

FIG. 2

Construction of the Plasmids pLA71, pLA72 and pLA73.

The insertion into the BamHI site of pJEM11 of BlaF* fragments (34) of 3 different lengths lead to the expression of fusion proteins with the phoA activity. Colorimetric assays were carried out according to the Brockman and Heppel technique (8), with p-nitrophenyl phosphate as substrate. The protein contents were measured with the aid of the Bio-Rad assay. The arbitrary alkaline phosphatase units (aU) were calculated as described in Materials and Methods.

FIG. 3

Western-Blot Analyses of PhoA Fusion Proteins.

Transformed *M. smegmatis* strains were cultured in Beck's medium containing kanamycin (20 µg/ml). Total extracts of sonicated bacteria were solubilized with SDS, resolved by SDS-PAGE and subjected to immunoblotting. The preparation of the rabbit anti-PhoA serum has been previously described (34). PhoA-coupled rabbit antibodies (Promega) and, as substrate, a mixture of X-P and nitro blue tetrazolium (BCIP-NBT, Promega) were used to reveal the PhoA fusions. Column 1: purified bacterial PhoA, *M. smegmatis* transformed by plasmids pJEM11: column 2, pLA71: column 3, pLA72: column 4, pLA73: column 5, pExp410: column 6, pExp53: column 7, pExp59: column 8, pExp421: column 9.

FIG. 4

Nucleotide Sequences and Deduced Amino Acid Sequences of Segments of Inserts Selected from the Plasmids pExp410, pExp53, pExp59 and pExp421.

The *M. smegmatis* clones with the alkaline phosphatase activity were selected on X-P/kanamycin dishes. Their plasmids were amplified in *E. coli* XL-1 B, and the nucleotide sequence of the inserts determined as described in Materials and Methods. A: pExp410 includes part of the 19 kDa lipoprotein. The reading frame is maintained at the junction with phoA (BamHI/Sau3A). B: pExp53 includes part of a gene exhibiting similarities with the 28 kDa *M. leprae* antigen. The divergent amino acids are in bold type. The codon for initiation of translation is GTG. The putative sites of cleavage by signal peptidase are indicated by arrows. C: pExp59 encodes a characteristic signal sequence. A putative ribosome-binding site (RSB) is underlined. The putative site of cleavage by signal peptidase is indicated by an arrow. D: pExp421 encodes conserved amino acid units conserved with proteins of the family of stearoyl-acyl carrier protein (ACP) desaturases. R. comm: R. communis (ricin).

FIG. 5

The Gene which is Similar to the Gene for the 28 kDa *M. leprae* Antigen is Present in a Single Copy in the *M. tuberculosis*, Genomo.

The *M. tuberculosis* genomic DNA was extracted according to standard procedures (27), digested with endonucleases PstI, SmaI, BstEII, SphI, BamHI and subjected to migration on a 1% agarose gel. The Southern-blot hybridization was carried out according to standard procedures (27). The 32P-labeled probe was a 180 bp PCR fragment of the pExp53 insert.

FIG. 6

Nucleotide sequence (IA (SEQ ID NO: 39) and IB (SEQ ID NO: 41)) and amino acid sequence (VIIIA (SEQ ID NO: 38) and VIIIB (SEQ ID NO: 40)) of the product of the IRSA gene encoding the *M. tuberculosis* P28 protein (two variants are presented). This gene is now designated by the abbreviation "erp" corresponding to the expression "exported repetitive protein".

FIG. 7

Preliminary nucleotide sequences flanking the *M. tuberculosis* IRSA gene.

FIG. 8

Bacteria genes for the regulation of iron (IRG's)

FIG. 9

Hydrophilicity profile of the *M. leprae* and *M. tuberculosis* P28 PROT2INS.

FIG. 10

A) Alignment of the nucleotide sequences of the gene encoding the *M. tuberculosis*, and *M. leprae* p28 proteins.

B) Alignment of the amino acid sequences of the *M. tuberculosis* and *M. leprae* p28 proteins.

FIG. 11

Construction of the Plasmids pJN3 and pJN11.

Only the relevant genetic elements and restriction sites are shown. The plasmids pRR3 and pJN1 have been described in the prior art (60) (58). The omega cassette was obtained by digestion of pHP45X with SmaI (59), followed by an agarose gel purification of a 2 kb fragment using the Geneclean kit (Bio 101 Inc.). Standard recombinant DNA techniques were used in accordance with the description given in the state of the art (61). In pJN3 and pJN11, the β lactamase (bla) gene has been interrupted. oriE and oriM designate the replication origins of pUC (*E. coli*) and of pAL5000 (mycobacteria), respectively.

FIG. 12

Structure of the Plasmids of the pJEM Series.

(A) In the schematic representation of the plasmids, only the relevant genetic elements are indicated. pJEM15 resulted from the cloning, into the ScaI site of pRR3, i) of a fragment obtained by PCR amplification (using OJN1: 5'- AAGCTTC-CGATTCGTAGAGCC-3' (SEQ ID NO: 10) and OJN2: 5'-GGGCTCGAGCTGCAG TGGATGACCTTTTGA-3' (SEQ ID NO: 11) as primers; and pJN11 as template) and containing tT4 and the N-terminal end of cII; ii) of the synthetic oligo-nucleotides corresponding to MCS1; and iii) the Hind III-DraI lacZ' fragment of pNM480. PJEM12-13-14 were obtained by cloning the PCR-amplified fragment described above, into the ScaI site of pRR3. The synthetic oligonucleotides corresponding to MCS2 were then inserted. Finally, each of the three forms of the pNM480 series were introduced into the Hind III site in MCS2. (B) Nucleotide sequences of the regions between the OJN1 primer and the 8th lacZ' codon (marked ****). These sequences were checked experimentally. The tT4 region is underlined and the synthetic RBS is in bold type. The amino acid sequence of the N-terminal end of cII is given under the DNA sequence. The HindIII sites are marked by an asterisk because they are not unique. For additional descriptions, see the legend in FIG. 11.

EXAMPLES

I) Identification of Genes Encoding Exported *M. tuberculosis* Proteins.

The results reported here describe the definition, for mycobacteria, of a genetic method of identification of exported proteins. This methodology is based on the translational fusion with bacterial alkaline phosphatase (PhoA). Such fusion proteins must be exported in order to have the PhoA activity (6, 13, 16). A PhoA gene was used after deletion of the promoter region, of the ribosome-binding site and of the entire region encoding the signal sequence whose codon for initiation of translation was used. Thus, the alkaline phosphatase activity is dependent on the translational fusion achieved in the correct reading frame with part of an exported protein. The construction of a phoA plasmid vector for mycobacteria is described first of all since it has been shown that the introduction, into this vector, of the gene for the exported *M. fortuitum* β-lactamase (blaF*) (34) leads to the production, in *M. smegmatis*, of fusion proteins having the PhoA enzymatic activity. A library of sequences for fusion between the *M. tuberculosis* genomic DNA and the phoA gene was then constructed. Twelve independent clones, which exported fusion proteins, were isolated. Among them, it was possible to identify the 19 kDa exported lipoprotein already described in *M. tuberculosis*, a new *M. tuberculosis* sequence exhibiting similarities with, the 28 kDa *M. leprae*, protein, a protein comprising conserved amino acid residues with stearoylacyl carrier protein (ACP) desaturases, and other new sequences.

Materials and Methods

Bacterial Strains, Plasmids, and Culture Conditions

The bacterial strains and the plasmids used in this study are presented in Table 1. The growth of *E. coli* and *M. smegmatis* strains, the electroporation, the screening on agar containing 20 µg/ml of kanamycin and 20 µg/ml of 5-bromo-4-chloro-3-indolyl phosphate (X-P) were performed as previously described (14)

*M. tuberculosis*, an isolate from a patient (strain 103), was cultured on solid Lowënstein-Jensen medium.

Manipulation and Sequencing of DNA

Manipulation of DNA and Southern-blot analyses were carried out with the aid of standard techniques (27). For the determinations of the sequences, the oligonucleotides (5-GGCCCGACGAGTCCCGC-3' (SEQ ID NO: 12) and 5'-TTGGGGACCCTAGAGGT-3' (SEQ ID NO: 13) were developed for sequencing across the fusion junctions of the *M. tuberculosis* inserts in pJEM11 (see below). The double-stranded plasmid DNA sequences were determined by the dideoxy chain termination method (28) using the T7 sequencing kit (Pharmacia) according to the manufacturer's instructions, or with the Taq Dyc Deoxy Cycle Terminator sequencing kit (Applied Biosystems), on a GeneAmp 9600 PCR system (Perkin Elmer), and passed over a DNA analysis system—Model 373 (Applied Biosystems).

Analyses of the Databanks

The nucleotide sequences were compared with those of the EMBL and GeneBank databanks using the FASTA algorithm (23) and the derived protein sequences were analyzed to determine a possible similarity with the sequences contained in the databanks for the PIR and SwissProt proteins using the BLAST algorithm (1).

Figure 2:
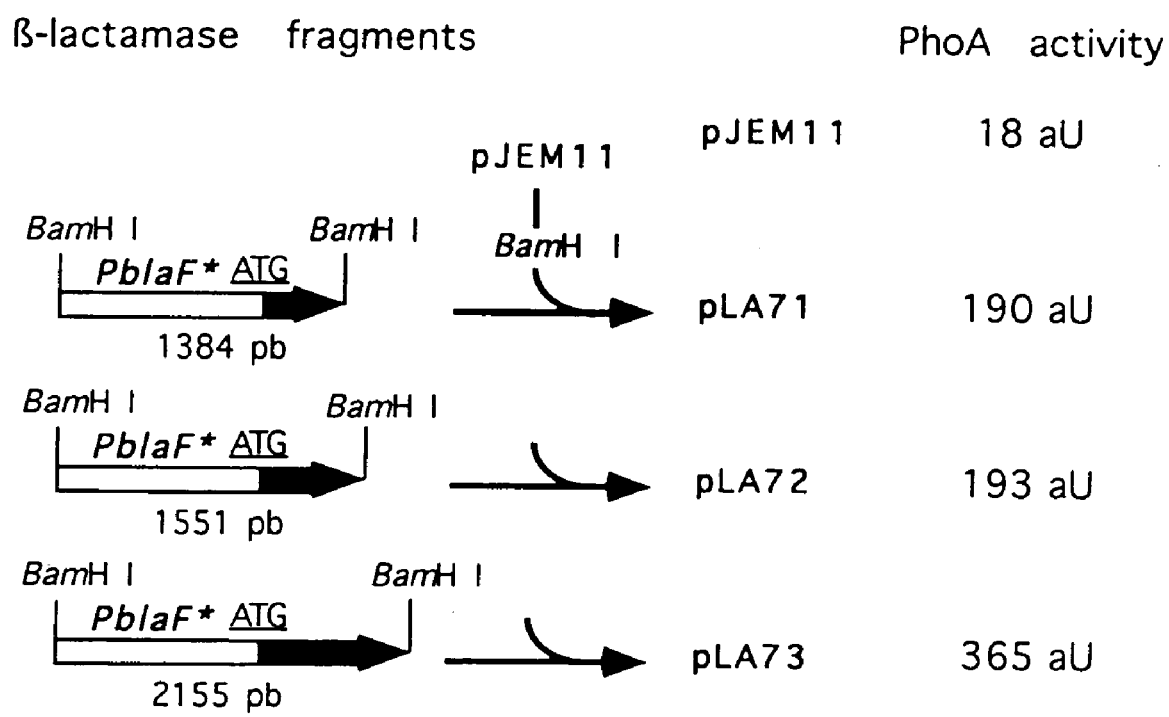

Constructions of the Plasmids pJEM11: The construction of pJEM11 is summarized in FIG. 1. Briefly, pJEM2 was constructed using the shuttle plasmid pRR3 of *E. coli*-mycobacteria (26), by insertion of the truncated lacZ fragment of pNM480 (18) a multiple cloning site or polylinker (MCS), and the transcriptional terminator of the omega cassette (24) The N-terminal EcoRV-KpnI fragment of lacZ is replaced with the truncated phoA fragment of pPHO7 (11), without initiation codon or signal sequence to give pJEM10. Finally, a potential initiation codon in the MCS was eliminated in order to give pJEM11.

pLA71, pLA72 and pLA73: Fragments of blaF* (34) of different length, obtained by PCR amplification, were inserted at the BamH1 site of pJEM11 to give pLA71, pLA72 and pLA73 (FIG. 2). The oligonucleotides (Genset, Paris) used for the PCR amplification were, upstream, 5'-CGG-GATCCTGCTCGGCGGACTCCCGG-3' (SEQ ID NO: 14) and, downstream, 5'-CGGGATCCGGTCATCGATCGGT-GCCGCCAA-3' (SEQ ID NO: 15), 5'-CGGGATCCCGC-CGTGCTCGOCCATCTGCAG-3' (SEQ ID NO: 16), and 5'-CGGGATCCAGAGTAAGGACGGCAGCACCAG-3' (SEQ ID NO: 17), for pLA71, pLA72 and pLA73 respectively. The PCR amplifications were carried out in a DNA Thermal Cycler (Perkin Elmer), using Taq polymerase (Cetus), according to the manufacturer's recommendations.

Construction of the *M. tuberculosis* Genomic Libraries

*M. tuberculosis* genomic DNA was extracted according to standard procedures (27). This DNA was partially digested with Sau3A (with 1 U per 2 µg) at 37° C. for 2 min 30 sec. The digestion was stopped by the addition of phenol. This DNA was then run on low-melting point agarose (Gibco, BRL). The fraction containing the fragments having from 400 to 2,000 bp was extracted with agarase (GELase, Epicentre Technologies) and ligated into the compatible BamHI site of pJEM11 with 74 DNA ligase (Boehringer Mannheim), at 16° C. overnight.

Assay of Alkaline Phosphatase

For the assays of alkaline phosphatase, *M. smegmatis* was cultured in L broth supplemented with 0.05% tylaxopol (Sigma) at 37° for 48 h. The alkaline phosphatase activity was assayed by the Brockman and Heppel method (8), in sonicated extracts as previously described (34), using p-nitrophenyl phosphate as substrate for the reaction. The protein contents were measured with the aid of the Bio-Rad assay (Bio-Rad). The alkaline phosphatase activity is expressed in arbitrary Units (aU)=$OD_{420} \times 10^5 \times 1$ g of protein$^{-1} \times$min$^{-1}$.

Preparations of Antibodies, SDS-Polyacrylamide Gel Electrophoresis and Immunoblottings The preparation of a rabbit anti-PhoA serum has been previously described (34). Cellular extracts of *M. smegmatis* were prepared by sonication, SDS-PAGE and immunoblotting were performed as previously described (36).

Results

Figure 1B:
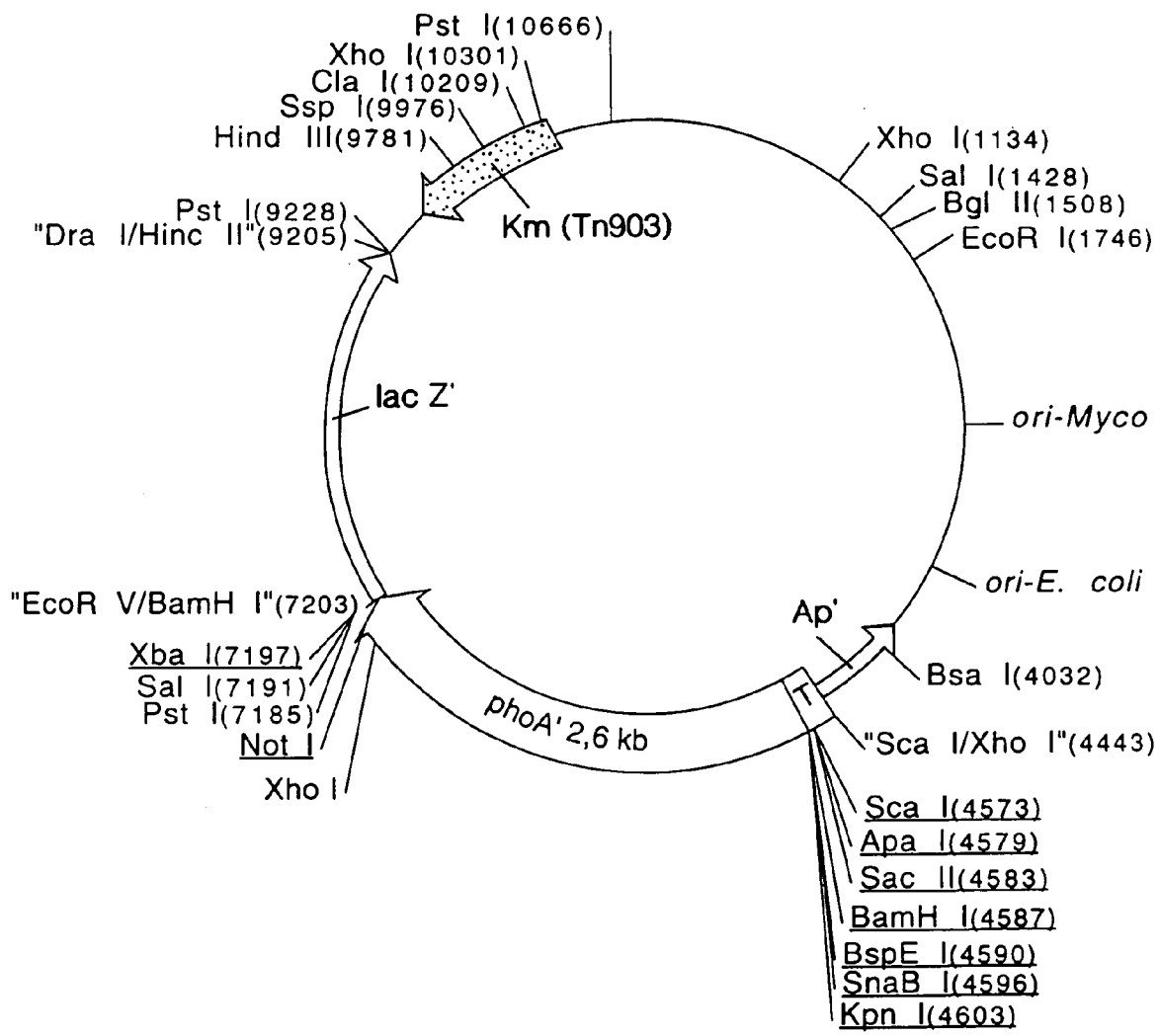

Construction of a Shuttle Plasmid Vector (pJEM11) for the Production of Fusion Proteins with PhoA in *M. smegmatis* pJEM11 has a truncated phoA gene of *E. coli* without initiation codon or any regulatory elements (FIG. 1). The multiple cloning site allows the insertion of fragments derived from genes encoding putative exported proteins at the same time as their regulatory elements. Thus, fusion proteins were able to be produced, they expressed the activity of alkaline phosphatase when the fusion was exported. pJEM11 is an *E. coli*/mycobacteria shuttle plasmid which includes the gene for resistance to the antibiotic kanamycin of tn903 as selectable marker.

Insertion of Genetic Elements Responsible for the Expression and Export of β-lactamase in pJMEM11 lead to the production of PhoA fusion proteins which are enzymatically active in *M. smegmatis*

Figure 3:

The three plasmids were constructed by insertion of fragments of different length derived from the β-lactamase gene of the overproducing strain *M. fortuitum* D316 (blaF*) (34) at the BamHI site of pJEM11 (FIG. 2). In pLA71, the 1384 bp fragment includes the promoter, the segment encoding the 32 amino acids of the signal sequence, and the first 5 amino acids of the mature protein (there is no Shine-Dalgarno sequence for ribosomal attachment in the original sequence of blaF*). pLA72 carries a 1550 bp fragment including the elements encoding the signal sequence and the first 61 amino acids of the mature protein. In pLA73, the 2155 bp fragment contains the whole blaF*. These plasmids were used to transform *M. smegmatis* and the transformants were screened for the enzymatically active PhoA fusions by plating on agar media containing kanamycin and X-P. X-P is soluble and is colorless, but after cleavage of the phosphate with alkaline phosphatase, a blue precipitate is produced. Thus, alkaline phosphatase-producing clones could be easily identified by their blue color. The expression of pLA71, 72 and 73 in *M. smegmatis*, leads to blue colonies, whereas colonies with pJEM11 remained white. Western-blot analyses showed the production of phoA fusion proteins with an apparent molecular weight of about 47.5 kDa, 54 kDa and 76 kDa, for pLA71, pLA72 and pLA73 respectively (FIG. 3, column 3, 4, 5). These molecular weights are in agreement with the length of the mature protein fused with alkaline phosphatase (apparent MW of 46 kDa, FIG. 3, column 1). In pJEM11, there is no expression of PhoA, as expected (FIG. 3, column 2). The assay of the alkaline phosphatase activity (see FIG. 2) of these bacteria confirms the expression of an enzymatic activity with the 3 pLA constructs. However, *M. smeqmatis* with pLA73 expresses an activity which is about twice as high compared with pLA73 and 72. In separate experiments, we have confirmed that the intracellular production of phoA under the control of a mycobacterial promoter, without fusion with an exported protein, was not associated with the expression of the alkaline phosphatase activity. All these results indicate that in this system, the activity of alkaline phosphatase depends on the translational fusion and the actual export of the product. Consequently, pJEM11 is suitable for the genetic identification of the proteins exported by mycobacteria.

Construction in *M. smegmatis* of a Bank of PhoA Fusions with *M. tuberculosis* Genomic DNA Fragments The genomic DNA of a clinical isolate of *M. tuberculosis* was purified and partially digested with Sau3A. The 400/2, 000 bp fraction was inserted at the compatible BamHI site of pJEM11. The ligation products were transferred into *E. coli* XL-1 blue by electroporation to obtain an amplification stage. About 2,500 clones containing plasmids with inserts grew on an agar medium containing kanamycin. The plasmids purified from the transformants were combined and transferred by electroporation into *M. smegmatis* MC$^2$155. The transformed bacteria were plated on L agar-kanamycin-X-P. About 14,000 clones were obtained. After incubating for 4 days, the first blue, and therefore PhoA*, colonies were observed. Each day, the dishes were checked, and new PhoA* colonies were isolated. The closed colonies were lyzed, and their DNA introduced by electroporation into *E. coli* XL-1 blue, for the preparations of plasmids. In all, 12 different inserts allowing the expression of phoA were isolated and sequenced. There sequences had similarities with known sequences.

Fusion of PhoA with the Gene for the 19 kDa *M. tuberculosis* Lipoprotein

One of the plasmids (pExp410) has an insert corresponding to part of the gene for the 19 kDa protein already known. This gene encodes an exported lipoprotein (5, 31). FIG. 4A shows the DNA sequence corresponding to the fusion between this gene and phoA. As expected, the same reading frame is maintained between the two proteins. The expected molecular weight of the fusion protein, according to the sequence, is thought to be close to 57 kDa. However, the true molecular weight observed by Western-blot analysis is identical to the purified PhoA protein (FIG. 3, column 1 and 6), which suggests that the fusion protein is cleaved near the PhoA junction.

Fusion with a Sequence Similar to the Gene for the 28 kDa *M. leprae* Protein

The 28 kDa *M. leprae* protein is a major antigen which is very often recognized by the sera from patients suffering from the lepromatous form of leprosy (9). In the *M. tuberculosis* insertion bank prepared, a sequence carried by a recombinant vector (pExp53), exhibiting 77% similarity with the nucleotide sequence of this gene and 68% for the deduced amino acid sequence (FIG. 4 B), was identified. In Western-blot analysis, the molecular weight of the fusion protein is about 52 kDa (FIG. 3, column 7), which provides for about 45 amino acids of the mycobacterial protein in the fusion protein, after cleavage of the signal peptide. This is in conformity with the length of the fragment of the *M. tuberculosis* gene fused with phoA (FIG. 4 B).

Figure 5:
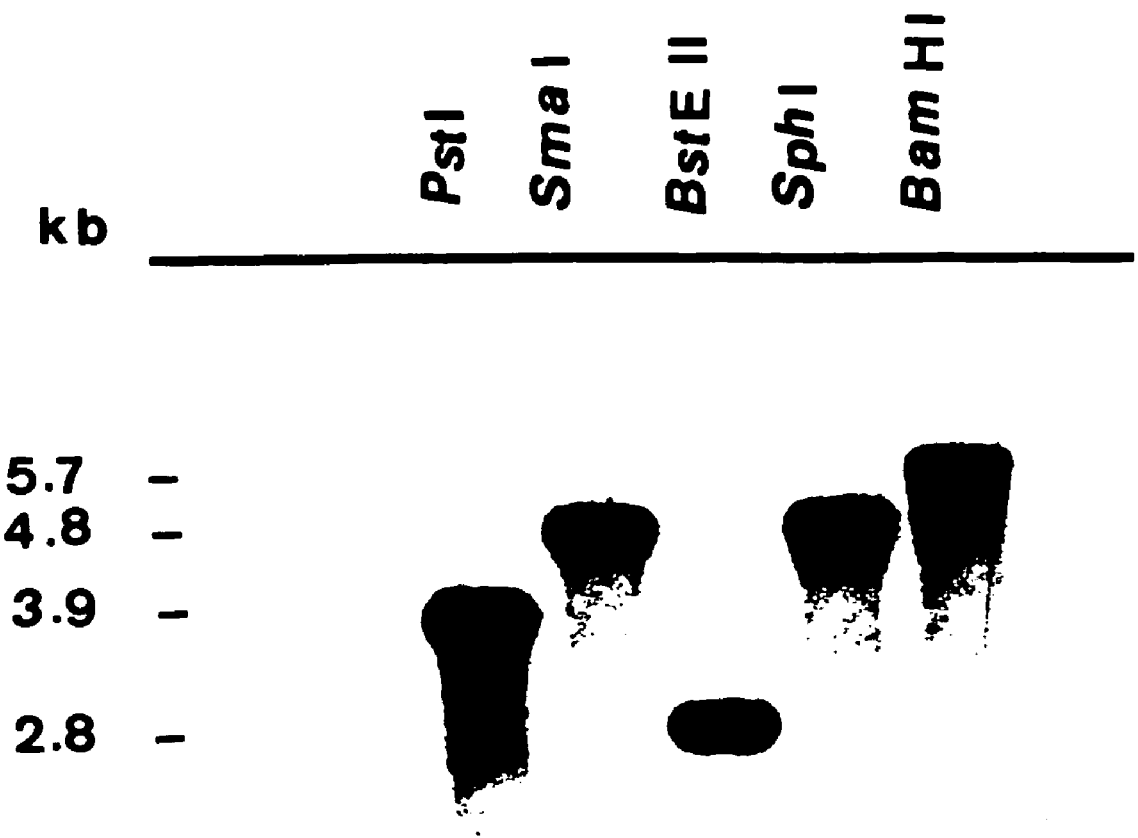
Figure 9:
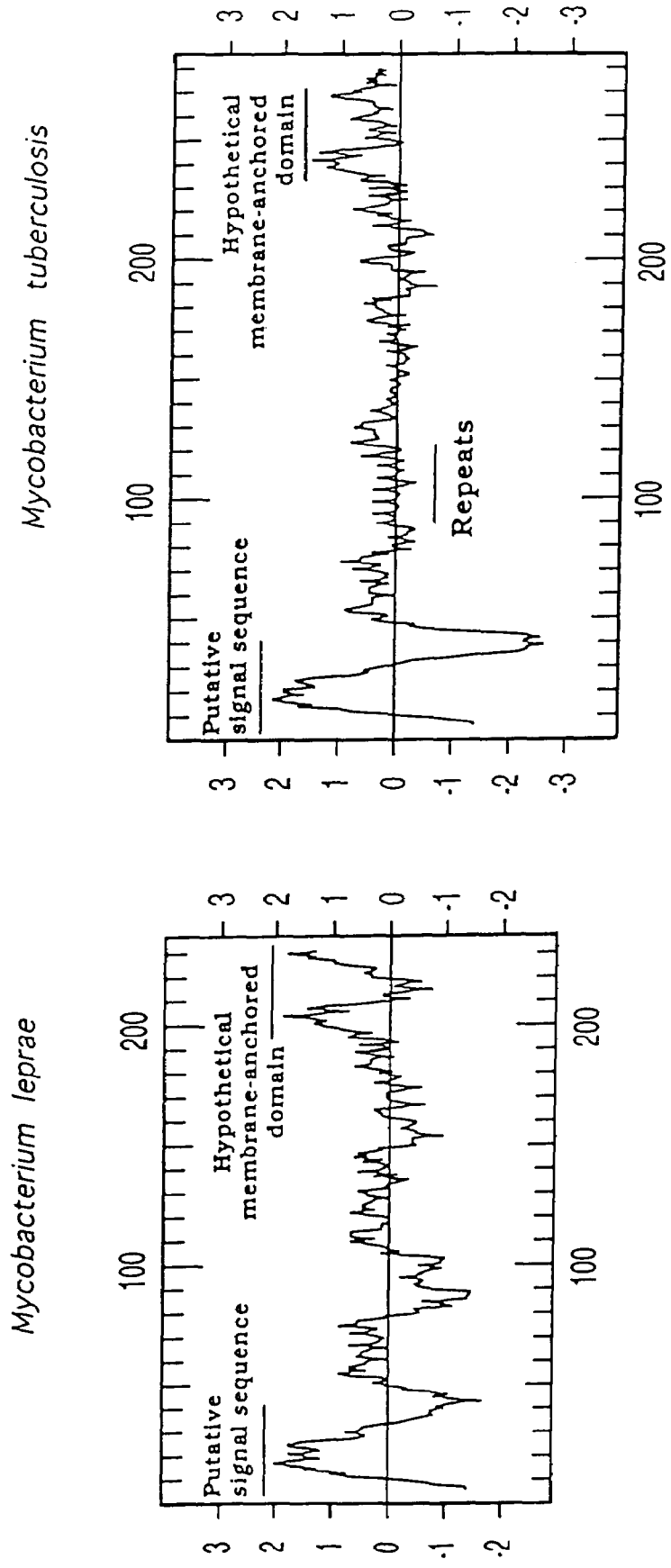

Southern-blot analyses of the *M. tuberculosis* genomic DNA were carried out. It was shown that a 180 bp fragment of the 2 kb insert of the plasmid pExp53 does not contain any restriction site for the endonucleases PstI, SmaI, BamHI, BstEII and SphI. This fragment was amplified by PCR. The *M. tuberculosis* genomic DNA was digested with the aid of these enzymes, and probed with the 32P-labeled PCR fragment. As can be seen in FIG. 5, only one band was observed when the genomic DNA was digested with each of the five enzymes, which suggests that the gene is present in only one copy in the *M. tuberculosis* genome.

Other PhoA Fusions Carrying the Putative Signal Sequences

FIG. 4C shows the sequence of an insert carried by a recombinant vector (pExp59) fused with phoA. It has a typical signal sequence allowing the export of proteins. The sequence presented is in conformity with the usual rules as established in Gram-negative bacteria (25). It contains two positively charged amino acids (Arg, Asn) after the initiation codon, followed by a hydrophobic peptide, with a Gly, probably corresponding to a loop in the three-dimensional structure of the peptide. A potential site of cleavage by signal peptidase is indicated by an arrow, which gives a fusion protein with a molecular weight close to that of phoA, as shown in FIG. 3, column 8, conformably.

PhoA Fusion Proteins with Amino Acid Units Conserved with Stearoyl-Acyl Carrier Protein (ACP) Desaturases The ACP-desaturases are enzymes involved in the pathways for the biosynthesis of fatty acids. In particular, these enzymes are integral membrane proteins (29). Analyses of the plasmid pExp421 of the prepared bank showed two amino acid units conserved with ACP-desaturases, one of 9 amino acids and the second of 14 amino acids (FIG. 4D). The rest of the sequence did not show any significant similarity with known proteins.

Discussion

More than 30 secreted proteins have been found in BCG or *M. tuberculosis* filtrates in the short term, with a minimum lysis of the bacterium (1,19, 38). These proteins have been classified according to their molecular weight and their immunological reactivities. Some were characterized more extensively. For example, the secreted proteins of the complex of antigen 85 (antigens 85 A, B and C) are 32 kDa proteins exhibiting serological cross-reactions (7, 35). The antigens 85 A and 85 B exhibit an affinity toward fibronectin and might be involved in the internalization of *M. tuberculosis* in the macrophages. The genes for these immunologenic proteins (7), and for 23 kDa proteins (MPB64) (37) and for 19 kDa proteins (5) have been cloned and sequenced and sequences of signal peptides characteristic of exported proteins have been found. The recombinant proteins produced using these genes are thought to be valuable tools for the serological diagnosis of tuberculosis. Superoxide dismutase (SOD) of 23/28 kDa is abundant in short term culture filtrates, and are thought to be involved in the survival of mycobacteria in the phagolysosome. The gene encoding SOD in *M. tuberculosis* has been closed and sequenced (39). Advantageously, no characteristic signal peptide sequence has been found. This suggests a specific route for secretion of this enzyme by mycobacteria. Secreted proteins in two narrow molecular weight ranges (6-10 kDa and 26-34 kDa) are major T cell antigens (3) and induce, in mice, T cell immune responses which are protective against a challenge with live mycobacteria of the *M. tuberculosis* complex (4). It has been suggested that the difference in the immune responses observed between live and killed bacteria are due to these exported/secreted proteins (20). These various preliminary results suggest that a better characterization of exported/secreted proteins of pathogenic bacteria of the *M. tuberculosis* complex might be highly useful both for understanding their pathogenicity and for developing new vaccines.

While secreted proteins have been studied by biochemical methods, other genetic methodologies might prove necessary. Using a truncated phoA gene, fusion systems have been developed which allow the attachment of the amino ends of other proteins onto PhoA. This approach is based on the *E. coli* periplasmic bacterial alkaline phosphatase. This enzyme must be located extracytoplasmically to be active. Thus, alkaline phosphatase may be used as subcellular localization probe.

A PhoA methodology has been developed and described here for the identification of proteins exported by mycobacteria the insertion of blaF* into pJEM11 leads to the production, in *M. smegmatis*, of fusion proteins with alkaline phosphatase activity. Furthermore, PhoA fusions with 3 different fragments of BlaF* were enzymatically active, which suggests that most of the fusions in phase with exported proteins will have a PhoA activity.

A bank of *M. tuberculosis* inserts in pJEM11 has been constructed and expressed in *M. smegmatis*. In this bank, part of the gene encoding the known exported lipoprotein of 19 kDa (pExp410) has been isolted. This *M. tuberculosis* protein is one of the serologically immunodominant antigens found in this bacillus. Analyses of the DNA sequence of the gene encoding this antigen indicate that the hydrophobic NH2-terminal region is a lipoprotein signal peptide (5). Part of this lipoprotein has been fused with the outer surface A protein of *Borrelia burgdorferi* to construct a recombinant BCG vaccine capable of inducing a high immune response (31).

Two other sequences sharing similarities with the exported or membrane proteins have also been identified:

pExp53 was shown to exhibit similarities with the gene for the 28 kDa *M. leprae* antigen this *M. leprae* antigen has been found by screening a λgt 11 library with serum from patients suffering from the lepromatous form of leprosy. It is a major antigen involved in the humoral immune response to *M. leprae* (9). Advantageously, it has been shown that a peptide of 20 amino acids of this protein exhibits considerable similarity with a peptide of the 19 kDa *M. tuberculosis* antigen, and it is an epitope of T cells exhibiting cross-reactions (12). The DNA sequence of the gene encoding the 28 kDa *M. leprae* antigen suggests that "the abovementioned amino acid sequence of the protein contains a potential signal peptide at its amino-terminal end and two long hydrophobic domains, which suggests that it is screened for localization on the bacterial plasma membrane or the cell wall" (9).

A fusion protein encoded by a plasmid of our bank (pExp421) is thought to share amino acid units with desaturases. The ACP-desaturases are enzymes involved in the pathways of the biosynthesis of fatty acids. In general, these enzymes are integral membrane proteins (39). This result suggests that is possible to have isolated part of a gene which is important in the metabolism of lipids in *M. tuberculosis*, maybe involved in the lipid cell wall biosynthesis pathway.

Another plasmid (pExp59) with a characteristic putative signal sequence has been found.

In conclusion, the results presented demonstrate that the technology of PhoA for the genetic identification of exported proteins may be successfully adapted for *M. tuberculosis*. Preliminary screenings of an insert bank giving PhoA fusion proteins have revealed sequences exhibiting similarities with known exported proteins.

II) Expression of the P28 *M. tuberculosis* Protein

BCG is a live vaccine. It is the only vaccine used to protect against tuberculosis. Its efficacy has proved variable according to the populations vaccinated, ranging from about 80% in Great Britain to 0% in India. It therefore seems essential to search for a more effective vaccine. Moreover, the use of a live vaccine currently poses problems because of the extension of the AIDS epidemic.

Several studies have shown that antigens exported by *Mycobacterium tuberculosis*, the agent for tuberculosis, had a protective effect against a challenge with the virulent strain. The studies reported here consisted in using a genetic method for isolating and studying the *M. tuberculosis* genes encoding exported proteins. We describe here the isolation and characterization of a gene encoding a protein having homologies with the 28 kDa *Mycobacterium leprae* protein already described.

Methodology for the Cloning of Genes Encoding Exported Proteins.

The methodology presented in detail in part I is based on the use of translational fusions with the gene encoding the *Escherichia coli* alkaline phosphatase, PhoA. Such fusion proteins have a detectable alkaline phosphatase activity only if they are exported. A plasmid vector carrying a phoA gene lacking its promoter, its ribosomal NRA-binding site and its signal sequence was constructed. Using this vector, a PhoA activity can be observed only after translational fusion in the correct reading frame with an exported protein. The vector, called pJEM11 has a replication origin for *E. coli* and another for mycobacteria. It also has a selectable marker, the kanamycin-resistance gene of the transposon Tn905. A multiple cloning site precedes the truncated phoA gene.

A genomic DNA library obtained from an *M. tuberculosis* strain (Mt103) isolated from a tuberculosis patient was constructed in pJEM11 by inserting DNA fragments derived from a partial hydrolysis by the enzyme Sau3a. The clones selected made it possible to identify a nucleotide fragment of the 28 kDa *M. tuberculosis* gene homologous to the gene encoding the 28 kDa *M. leprae* protein.

In the lepromateous patients, antibodies directed against this 28 kDa protein are observed, suggesting that this protein is an immunodominant antigen. It was hypothesized that in *M. tuberculosis*, the 28 kDa protein possessing homologies with the 28 kDa *M. leprae* protein could also be an immunodominant antigen and that it could serve in the construction of specific immunological tests allowing the detection of the tuberculosis infection or of the tuberculosis disease. It could perhaps be used for the construction of subunit vaccines in different vaccine preparations. Furthermore, it could be useful as vector for the expression of antigens in mycobacteria for the construction of recombinant vaccines.

Cloning and Sequencing of the Gene Encoding a 28 kDa *M. tuberculosis* Protein

Using the insert contained in the plasmid pExp53 as probe, the whole gene encoding the 28 kDa *M. tuberculosis* protein was cloned by colony hybridization of an *M. tuberculosis* DNA library constructed by inserting *M. tuberculosis* DNA fragments of between 2 and 6 kb in size, obtained by total hydrolysis with the enzyme PstI into the vector pBluescript KS-. The *M. tuberculosis* PstI fragment corresponding to the positive clone and comprising a 4.1 kb insert was sequenced. FIG. 10 shows the nucleotide sequence of the fragment and the similarities with the gene encoding the 28 kDa *M. leprae* protein. The sequence of the 28 kDa *M. tuberculosis* gene is, like that of *M. leprae*, preceded by a sequence possessing similarities with the "iron" boxes found upstream of the genes expressed during an iron deficiency. An iron deficiency situation is encountered during growth in vivo. It is hypothesized that the expression of this gene is induced during the growth, in the macrophages, of the mycobacteria harboring this gene. Furthermore, the 28 kDa *M. tuberculosis* protein possesses, in its central part, two regions containing units of 5 amino acids repeated in tandem, which are absent from the homologous *M. leprae* protein. Analogous repeated structures have been previously identified in major antigens present at the surface of other bacterial or parasitic pathogenic agents such as the M protein (40) of the Streptococcacea and the CS protein of the Plasmodiae (41).

All or part of the 28 kDa *M. tuberculosis* protein, whose gene sequence is presented here, could be a potential protective antigen for the construction of a tuberculosis vaccine. Such an antigen may be obtained by purification from cellular extracts of *M. tuberculosis* or from cellular extracts of genetically recombined heterologous organisms. Furthermore, the 28 kDa *M. tuberculosis* protein, or peptides derived therefrom, could be an antigen capable of being used in ELISA tests for screening tuberculosis patents.

By using the 28 kDa *M. tuberculosis* gene as probe, hybridization under conditions of high stringency was observed only with the genomic DNA of strains belonging to the *M. tuberculosis* complex consequently, the sequence corresponding to the 28 kDa *M. tuberculosis* gene is a specific sequence which may be used for tests for detection of the tuberculosis bacilli, using DNA or RNA probes and in vitro methods of gene amplification.

The regulatory region and the 28 kDa *M. tuberculosis* gene may be used as carrier molecules to express heterologous antigens in BCG or any other mycobacterial vector useful for the construction of vaccines.

III) Expression of Mycobacteria Genes; Evaluation of Different Expression Promoters An important aspect of the results obtained relates to the construction of genetic tools for studying the expression of genes in mycobacteria. Regulatory sequence-probe vectors have been used in the prior art to isolate and analyze regulatory sequences in a large number of bacteria (54). The definition, by the inventors, of such tools specific to mycobacteria facilitates the study of the genetic mechanisms regulating virulence in the pathogenic species, and the isolation of new regulatory sequences which might be useful for developing improved recombinant BCG vaccines.

Initially, the expression of mycobacterial genes was studied in heterologous systems, *Escherichia coli* and *Streptomyces lividans* (46) (51) (60). These analyses suggest that most of the mycobacterial genes are more efficiently expressed in *S. lividans* than in *E. coli*. Subsequently, vectors based on mycobacterial plasmids were constructed which might be used for studies in homologous systems. The vectors pYUB75 and pYUB76 were designed to select gene fusions with a truncated *Escherichia coli* lacZ gene (42). the plasmid pSD7 allows the construction of fusions of operons with a gene for chloramphenicol acetyltransferase (CAT) without promoter (47). By using these vectors a number of mycobacterial regulatory sequences were isolated and evaluated both in *E. coli* and in *Mycobacterium smegmatis*.

The inventors have described other constructions of vectors of the pJEM series, which have several advantages: they carry a transcription terminator, suitable multiple cloning sites, and they allow fusions both of operons and of genes with lacZ. lacZ was chosen as reporter gene because the enzyme encoded, β-galactosidase, remains active when heterologous sequences are fused with its amino-terminal end (45) (64). Its activity may be easily measured in vitro, even at very low levels with the aid of fluorescent compounds (48). β-Galactosidase is also highly immunogenic. It induces both humoral and cellular immune responses after presentation to the mouse immune system by recombinant bacteria (44) (56). Thus, β-galactosidase may also be used as reporter of the immunogenicity of a recombinant vaccine. By using pJEM vectors, new regulatory sequences active in BCG could be isolated and the recombinant BCG strains easily tested for their capacity to induce immune responses in mice.

A comparative study of the activities of various promoters in *M. smegmatis* and BCG was also made. The results suggest that the RNA polymerases of *M. smegmatis* and of BCG do not share the same specificity.

The construction of pJEM vectors. Ideally, a plasmid vector promoter-probe should contain five elements:

a replicon, ii) a selectable marker, and a reporter cassette containing iii) a transcription terminator followed iv) by multiple cloning sites (MCS) and v) a reporter gene lacking its regulatory sequences.

To construct a promoter cloning vector, mycobacteria, the replicon derived from the plasmid pAL5000 of *Mycobacterium fortuitum*, and the kanamycin resistance gene (aph) of Tn903 (58) were used. These genetic elements are basic components of most plasmids currently used for the transformation of mycobacteria. They appear to confer high stability on transformed clones of *M. smegmatis* and *M. bovis* BCG both in vitro and in vivo (in mice) even in the absence of selection by antibiotics (56). To facilitate the preparation and manipulation of episomal DNA, most of these plasmids also contain an *E. coli* replicon. Thus, we chose the plasmid pRR3, an *E. coli*-mycobacteria shuttle vector which contains these three genetic elements as basic vector (58).

Figure 11:
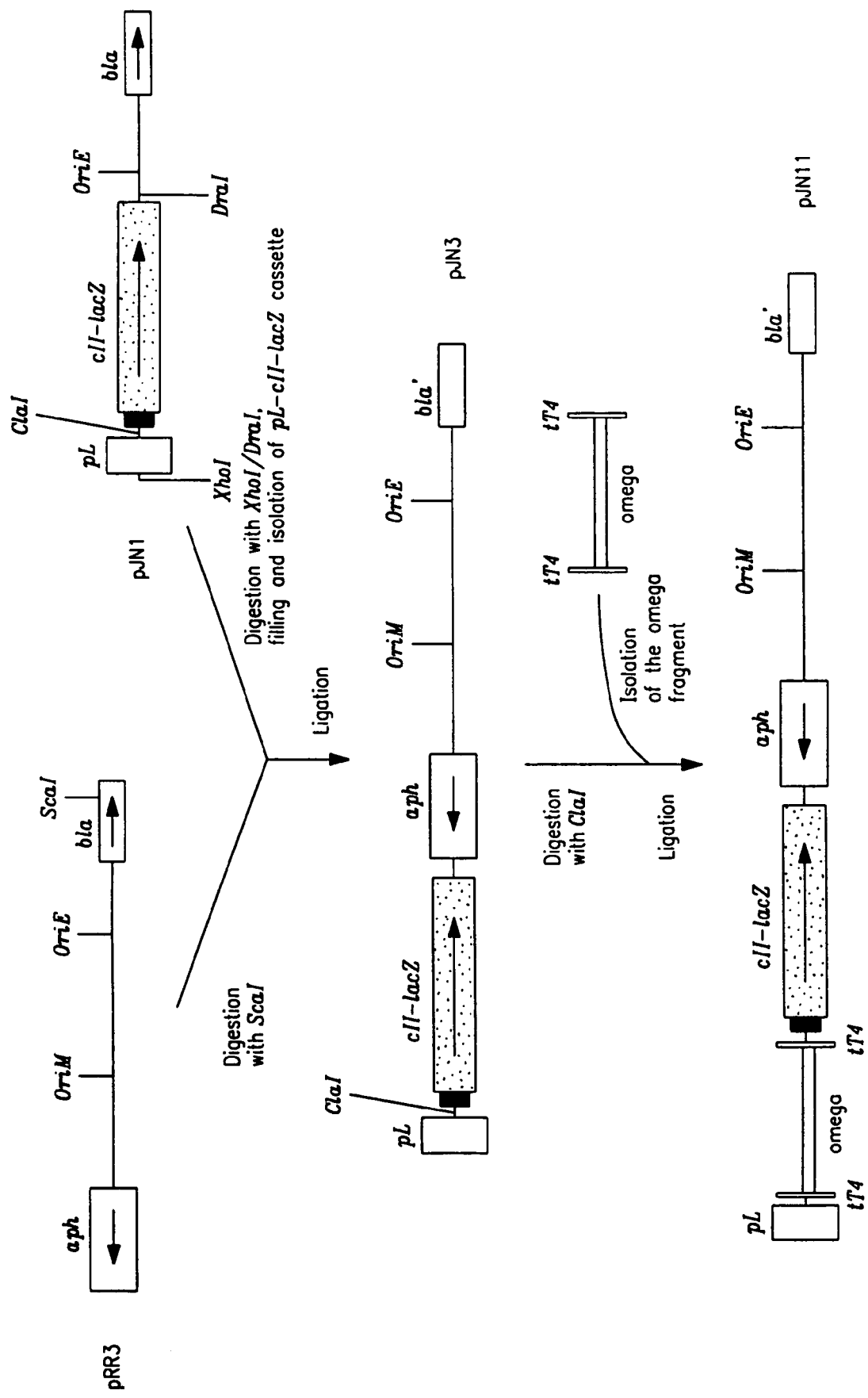

No mycobacterial transcription terminator has yet been characterized. To examine if the T4 coliphage transcription terminator (tT4) was active as termination site for the mycobacteria RNA polymerases, the omega interposon (57) was cloned into the plasmid pJN3, upstream of the SRBS-cII-lacZ element, generating pJN11 (FIG. 11). The omega fragment is composed of a streptomycin/spectinomycin resistance gene flanked by short inverted repeats containing tT4. The insertion of omega into a DNA fragment leads to termination of the synthesis of RNA in E. coli (57). pJN3 was constructed by cloning, into the ScaI site of pRR3, a cassette composed of a truncated lacZ combined with a synthetic RBS (sRBS) and the 5' end of the lambda phage cI regulatory gene and the pL promoter (FIG. 11). M. smegmatic mc2155 (61) was transformed with pJN3 (pL-sRBS-cII-lacZ) or pJN11 (pL-X-sRBS-cII-lacZ) by electroporation and the transformant clones were identified after growth on LB-XgaI plates. The transformant clones carrying pJN3 gave blue colonies and the transformant clones carrying pJN11 gave white colonies. The β-galactosidase activity in M. smeqmatis (pJN11) was 50 times as low as that in M. smegmatis (pJN3) (Table 2). Thus, tT4 contained in the insert X acts as an efficient transcription terminator in M. smegmatis.

A DNA fragment containing the tT4 segment followed by the sRBS-cII-lacZ element of pJN11 was synthesized in vitro by amplification by PCR and an MCS (MCS1), containing 6 unique restriction sites, was added. The resulting cassette was then cloned into the ScaI site of pRR3, giving the operon fusion vector pJEM15 (FIG. 12). The electroporation of M. smegmatis $MC^2155$ and of BCG with this plasmid led to white colonies on LB-XgaI plates with a very weak β-galactosidase activity (Table 2). On the other hand, in E. coli, pJEM15 expressed a higher β-galactosidase activity, and consequently a blue color on LB-XgaI plates. This is probably due to its high color number. In E. coli, pUC vectors are present at a high copy number (greater than 500), whereas in mycobacteria, the replicon-derived plasmids pAL5000 have a copy number of approximately 3 to 10 (50). The testing of DNA fragments for promoter activity, with the aid of pJEM15, by blue-white screening, should thus be carried out directly in mycobacteria.

To obtain vectors allowing fusions of genes with lacZ, we followed a similar strategy. The three forms of truncated lacZ of the pNM480 series (55), which differ from each other in the "placing in translational phase" of a HindIII site located at its 5' end, were cloned, downstream of tT4 and of an MCS (MCS2) containing 7 unique restriction sites, into the ScaI site of pRR3. The resulting plasmids pJEM12-13-14 (FIG. 12) thus allow the cloning of a wide range of restriction fragments in phase with lacZ.

Evaluation of various promoters in M. smegmatis and BOG. Operon fusions between the cII-lacZ reporter cassette of pJEM15 and the promoters pAN (56), pblaF* (63), psu13 (52) and pgroES/EL1 (49) were constructed. The activity of these promoters was evaluated in M. smegmatis and in M. bovis BCG. The first three promoters were isolated from mycobacterial species: pblaF* is a high expression mutant of pblaF, which directs the expression of the M. fortuitum β-lactamase gene; pAN is an M. paratuberculosis promoter and psu13 a component of a mobile genetic element of M. fortuitum Tn610. These promoters were localized on the basis of the mapping of sites of initiation of transcription (pblaF* and pAN) or by deletion analysis (psu13) (62). pgroES/EL1 is a Streptomyces albus promoter which regulates the expression of the groES/EL1 operon, and is active both in M. smegmatis and BCG (65).

The cloning experiments were carried out directly in M. smegmatis. DNA fragments containing each of the promoters were isolated and inserted at MCS1 of pJEM15 disgested with the appropriate restriction enzymes. The resulting litigation mixtures were used to transform M. smegmatis mc2155 by electroporation and blue colonies were selected in order to electroduce E. coli MC1061 (45) as described above (43). The plasmids were isolated from these E. coli clones and analyzed. Those corresponding to the desired constructs pJN29 to pJN32 (table 2) were used for the electroporation of BCG (Pasteur strain).

The β-galactosidase activity was assayed on sonicated extracts of M. smegmatis and of BCG (table 2). The activity of the promoters varied considerably both between the promoters in a mycobacterial host and between the hosts for each promoter. The relative strength of these promoters was not the same in M. smegmatis and BCG. Although pblaF* was the most powerful promoter both in M. smegmatis and in BCG, the situation is different for the other promoters: pAN and pgroES/EL1 were more active than psul3 in BCG, but in M. smeqmatis, psul3 was more active than pAN or pgroES/EI1.

Das Gupta and his collegues (47) screened M. smegmatis and M. tuberculosis DNA libraries for the promoter activity in M. smegmatis. They reported a promoter frequency 10 to 20 times higher in the M. smegmatis DNA. Furthermore, very active promoters were more rare in the M. tuberculosis DNA libraries than in those of M smegmatis. These authors suggested that the M. tuberculosis promoters may have diverged considerably from those of M. smegmatis. The results presented here suggest that the transcriptional machinery of M. smegmatis and of M. bovis BCG, a species clearly related to M. tuberculosis, may be different.

In conclusion, the family of vectors constructed facilitates the study of the expression of genes in mycobacteria. A wide range of fragments may be easily cloned in phase with lacZ' (fusion of genes) or upstream of cII-lacZ (fusion of operons) and evaluated for the promoter activity by blue-white screening of mycobacterial transformants on LB-XgaI plates. The activity of these promoters may also be measured (by assaying the β-galactosidase activity), their sequences determined, and their site for initiation of transcription mapped (by primer extension analysis) using the "universal primer" or relates sequences (53) as primer.

IV) Expression of the ERP Protein in Recombinant Form in E. coli

The ERP protein was expressed in recombinant form in E. coli and purified by affinity chromatography. Two types of fusions between ERP and peptide fragments having a high affinity for specific chromatographic supports (Amylose, MalE system; chelated Nickel ($Ni^{2+}$), for the Histidine system) were carried out. They are:

ERP lacking its signal sequence fused at the C-ter with the maltose-binding protein (MalE) of E. coli (MalE-ERP);

ERP lacking its signal sequence ($ERP(His)_6$ ss) or in its entirety ($ERP(His)_6$), and possessing 6 C-ter Histidine amino acids.

After purification, analysis of these three fusion proteins by SDS-PAGE electrophoresis indicates that the ERP polypeptide possesses a relative molecular weight (MW) of 36 kDa. There is a major difference between the MW calculated from the sequence (28 kDa) and the MW observed experimentally (36 kDa). This delay in the electrophoretic migration could be due to the high content of Proline residues, or from post translational modifications.

REFERENCES

1. Altschul, S. F. et al., 1990, J. Mol. Biol., 215: 403-410.
2. Andersen, P. et al., 1991, Infect. Immun. 59: 1905-1910.
3. Andersen, P. et al., 1991, Infect. Immun. 59: 1558-1563.
4. Andersen, P. et al., 1994, Imun. 62: 2536-2544.
5. Ashbridge, K. R. et al., 1989, Nucl. Acid. Res. 17: 1249.
6. Boquet, P. et al., 1987, J. Bacteriol. 169: 1663-1669.
7. Borremans, M. et al., 1989, Infect. Immun. 57: 3123-3130.

8. Brockman, R. W. et al., 1968, Biochemistry 7: 2554-2561.
9. Cherayil, B. et al., 1988, J. Immunol. 12: 4370-4375.
10. Gaillard, J. -L. et al., 1991, Cell 65: 1127-1141.
11. Gutierrez, C. et al., 1989, Nucl. Acids. Res. 17: 3999.
12. Harris, D. P. et al., 1991, J. Immunol. 147: 2706-2712.
13. Hoffman, C. S. et al., 1985, Proc. Natl. Acad. Sci. USA 82: 5107-5111.
14. Isberg, R. R. et al., 1987, Cell 50: 76 778.
15. Knapp, S. et al., 1988, J. Bact. 170: 5059-5066.
16. Manoil, C. et al., 1990, J. Bacteriol. 172: 515-518.
17. Miller, V. L. et al., 1987, cell. 48: 271-279.
18. Minton, N. P., 1984, Gene. 31: 269-273.
19. Nagal, S. et al., 1991, Infect. Immun. 59: 372-382.
20. Orme, I. M., 1988, Infect. Immun. 56: 3310-3312.
21. Orme, I. M. et al., 1993, J. Infect. Disea. 167: 1481-1497.
22. Pearce, B. J. et al., 1993, Mol. Microbiol. 9: 1037-1050.
23. Pearson, W. R. et al., 1988, Proc. Natl. Acad. Sci. USA. 85: 2444-2448.
24. Prentki, P. et al., 1984, Gene. 29: 303-313.
25. Pugsley, A. P., 1993, Microbiol. Rev. 57: 50-108.
26. Ranes, L. G. et al., 1990, J. Bacteriol. 172: 2793-2797.
27. Sambrook, J. et al., 1989, Molecular Cloning: a Laboratory Manual, $2^{nd}$ ed. Cold Spring Harbor Laboratory Press, Cold Spring Harbor, N.Y.
28. Sanger, F. et al., 1977, Proc. Natl. Acad. Sci. USA 74: 5463-5467.
29. Shanklin, J. et al., 1991, Proc. Natl. Acad. Sci. USA 88: 2510-2514.
30. Snapper, S. B. etal., 1990, Mol. Microbiol. 11: 1911-1919.
31. Stover, K. C. et al., 1993, J. Exp. Med. 178: 197-209.
32. Taylor, R. K. et al., 1987, Proc. Natl. Acad. Sci. USA 84: 2833-2837.
33. Taylor. R. K. et al., 1989, J. Bact. 171: 1870-1878.
34. Timm, J. et al., 1994, Microbiol. 12: 491-504.
35. Wiker, H. G. et al., 1992, Microbiol. Rev. 56: 648-661.
36. Winter, N. et al., 1991, Gene. 109: 47-54.
37. Yamaguchi, R. et al., 1989, Infect. Immun. 57: 283-288.
38. Young, D. B. et al., 1992, Mol. Microbiol. 6: 133-145.
39. Zhang, Y. et al., 1991, Mol. Microbiol. 5: 381-391.
40. Hollingstead S. et al., 1986, J. Biol. Chem. 262: 1677-1686.
41. Zavala, F. et al., J. Exp. Med. 157: 194-1957.
42. Barletta, R. G. et al., 1992, J. Gen. Microbiol. 138: 23-30.
43. Baulard, A. et al., 1992, Nucleic Acids Res. 20: 4105.
44. Brown, A. et al., 1987, J. Infect. Dis. 155: 86-92.
45. Casabadan, M. J. et al., 1980, J. Bacteriol. 143: 971-980.
46. Clark-Curtiss, J. E. et al., 1985, J. Bacteriol. 161: 1093-1102.
47. Das Gupta, S. K. et al., 1993, J. Bacteriol. 175: 5186-5192.
48. Garcia-del-Portillo, F. et al., 1992, Mol. Microbiol. 6: 3289-3297.
49. Guglielmi, G. et al., 1993, Basic and Applied Genetics. Americain Society for Microbiology, Washington, D.C.
50. Hatfull, G. H. et al., 1993, Genetic transformation of mycobacteria. TIM 1: 310-314.
51. Kieser, T. et al., 1986, J. Bacteriol. 168: 72-80.
52. Martin, C. et al., 1990, Nature 345: 739-743.
53. Messing, J., 1983, New M13 vectors for cloning, p. 20-78. In R. Wu, L. Grossman and K. Moldave (eds.), Methods in Enzymology, Academic Press, New York.
54. Miller, J. H., 1991, Bacterial Genetic Systems, In J. N. Abelson and M. I. Simon (eds.), Methods in Enzymology, Academic Press, San Diego.
55. Minton, N. P., 1984, Gene 31: 269-273.
56. Murray, A. et al., 1992, Mol. Microbiol. 6: 3331-3342.
57. Prentki, P. et al., 1984, Gene 29: 303-313.
58. Ranes, M. G. et al., 1990, J. Bacteriol. 172: 2793-2797.
59. Sambrook, J. et al., 1989, Molecular cloning: a laboratory manual, $2^{nd}$ ed. Cold Spring Harbor Laboratory Press, Cold Spring Harbor, N.Y.
60. Sirakova, T. D. et al., 1989, FEMS Microbiol. Lett. 59: 153-156.
61. Snapper, S. B. et al., 19 [illegible]0, Mol. Microbiol. 4: 1911-1919.
62. Timm, J. et al. Unpublished data.

TABLE 1

| Strain/Plasmid | Relevant characteristics | Reference |
| --- | --- | --- |
| E. coli XL1 - Blue | sup E44 hsdR17 recA1 gyrA46 thi relAl lac F' | 27 |
| M. smegmatis mc²155 | High-transformant mutant of M. smegmatis ATCC607 | 30 |
| pRR3 | E. coli-mycobacteria shuttle vector | 26 |
| pPH07 | pUC derivative carrying a truncated phoA gene | 11 |
| pNM480 | pUC derivative carrying a truncated lacz gene | 18 |
| pJEM11 | E. coli-mycobacteria shuttle vector carrying a truncated phoA gene | this work |
| pLA71 | pJEM11 in which has been cloned a 1,384 bp fragment from blaF* | 34, this work |
| pLA72 | pJEM11 in which has been cloned a 1,550 bp fragment from blaF* | 34, this work |
| pLA73 | pJEM11 in which has been cloned the complete blaF* | 34, this work |
| pExp410 | pJEM11 in which has been cloned part of the M. tuberculosis 19 kDa antigen gene | this work |
| pExp53 | pJEM11 in which has been cloned part of a M. tuberculosis gene similar to the M. leprae 28 kDa antigen gene | this work |
| pExp59 | pJEM11 in which has been cloned the signal sequence of a M. tuberculosis unidentified gene | this work |
| pExp421 | pJEM11 in which has been cloned a M. tuberculosis gene encoding a protein with amino acids motives similar to desaturases | this work |

The invention claimed is:

1. A purified antibody, which binds with a polypeptide consisting of SEQ ID NO: 39 or SEQ ID NO: 41, wherein the antibody does not bind with *M. leprae* P28 protein.

2. The purified antibody according to claim 1, wherein the antibody is a monoclonal antibody.

3. The purified antibody according to claim 1, wherein the antibody is a polyclonal antibody.

4. A purified antibody, which binds with a polypeptide consisting of a fragment of SEQ ID NO: 39 or SEQ ID NO: 41, wherein the antibody does not bind with *M. leprae* P28 protein.

5. The purified antibody according to claim 4, wherein the antibody is a monoclonal antibody.

6. The purified antibody according to claim 4, wherein the antibody is a polyclonal antibody.

7. A purified antibody according to claim 1, which binds with a peptide consisting of SEQ ID NO: 39.

8. A purified antibody according to claim 1, which binds with a peptide consisting of SEQ ID NO: 41.

9. A purified monoclonal antibody according to claim 2, which binds with a peptide consisting of SEQ ID NO: 39.

10. A purified monoclonal antibody according to claim 2, which binds with a peptide consisting of SEQ ID NO: 41.

* * * * *

SEQUENCE LISTING (1) GENERAL INFORMATION:

(iii) NUMBER OF SEQUENCES: 63

(2) INFORMATION FOR SEQ ID NO: 1:

-continued

```
    (i) SEQUENCE CHARACTERISTICS:
        (A) LENGTH: 5 amino acids
        (B) TYPE: amino acid
        (C) STRANDEDNESS: <Unknown>
        (D) TOPOLOGY: not relevant (ii) MOLECULE TYPE: peptide (xi) SEQUENCE DESCRIPTION: SEQ ID NO: 1:

Pro Gly Leu Thr Ser
1               5

(2) INFORMATION FOR SEQ ID NO: 2:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: not relevant (ii) MOLECULE TYPE: peptide (xi) SEQUENCE DESCRIPTION: SEQ ID NO: 2:

Pro Gly Leu Thr Asp
1               5

(2) INFORMATION FOR SEQ ID NO: 3:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: not relevant (ii) MOLECULE TYPE: peptide (xi) SEQUENCE DESCRIPTION: SEQ ID NO: 3:

Pro Gly Leu Thr Pro
1               5

(2) INFORMATION FOR SEQ ID NO: 4:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: not relevant (ii) MOLECULE TYPE: peptide (xi) SEQUENCE DESCRIPTION: SEQ ID NO: 4:

Pro Ala Leu Thr Asn
1               5

(2) INFORMATION FOR SEQ ID NO: 5:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: not relevant (ii) MOLECULE TYPE: peptide (xi) SEQUENCE DESCRIPTION: SEQ ID NO: 5:

Pro Ala Leu Thr Ser
1               5

(2) INFORMATION FOR SEQ ID NO: 6:
```

```
    (i) SEQUENCE CHARACTERISTICS:
        (A) LENGTH: 5 amino acids
        (B) TYPE: amino acid
        (C) STRANDEDNESS: <Unknown>
        (D) TOPOLOGY: not relevant (ii) MOLECULE TYPE: peptide (xi) SEQUENCE DESCRIPTION: SEQ ID NO: 6:

Pro Ala Leu Gly Gly
1               5

(2) INFORMATION FOR SEQ ID NO: 7:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: not relevant (ii) MOLECULE TYPE: peptide (xi) SEQUENCE DESCRIPTION: SEQ ID NO: 7:

Pro Thr Gly Ala Thr
1               5

(2) INFORMATION FOR SEQ ID NO: 8:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: not relevant (ii) MOLECULE TYPE: peptide (xi) SEQUENCE DESCRIPTION: SEQ ID NO: 8:

Pro Thr Gly Leu Asp
1               5

(2) INFORMATION FOR SEQ ID NO: 9:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: not relevant (ii) MOLECULE TYPE: peptide (xi) SEQUENCE DESCRIPTION: SEQ ID NO: 9:

Pro Val Gly Leu Asp
1               5

(2) INFORMATION FOR SEQ ID NO: 10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"
    (xi) SEQUENCE DESCRIPTION: SEQ ID NO: 10:

AAGCTTCCGA TTCGTAGAGC C                                               21

(2) INFORMATION FOR SEQ ID NO: 11:
```

```
    (i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO: 11:

GGGCTCGAGC TGCAGTGGAT GACCTTTTGA                                      30

(2) INFORMATION FOR SEQ ID NO: 12:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO: 12:

GGCCCGACGA GTCCCGC                                                    17

(2) INFORMATION FOR SEQ ID NO: 13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO: 13:

TTGGGGACCC TAGAGGT                                                    17

(2) INFORMATION FOR SEQ ID NO: 14:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO: 14:

CGGGATCCTG CTCGGCGGAC TCCGGG                                          26

(2) INFORMATION FOR SEQ ID NO: 15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO: 15:

CGGGATCCGG TCATCGATCG GTGCCGCGAA                                      30
```

(2) INFORMATION FOR SEQ ID NO: 16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO: 16:

```
CGGGATCCCG CCGTGCTCGG CCATCTGCAG                              30
```

(2) INFORMATION FOR SEQ ID NO: 17:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO: 17:

```
CGGGATCCAG AGTAAGGACG GCAGCCACCA G                            31
```

(2) INFORMATION FOR SEQ ID NO: 18:

(i) SEQUENCE CHARACTERISTICS:
        (A) LENGTH: 27 base pairs
        (B) TYPE: nucleic acid
        (C) STRANDEDNESS: double
        (D) TOPOLOGY: circular (ii) MOLECULE TYPE: other nucleic acid (ix) FEATURE:
        (A) NAME/KEY: CDS
        (B) LOCATION: 1..15

(xi) SEQUENCE DESCRIPTION: SEQ ID NO: 18:

```
AGC CAC TAC AAG ATC CGGATACGTA CG                             27
Ser His Tyr Lys Ile
  1               5
```

(2) INFORMATION FOR SEQ ID NO: 19:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 19:

```
Ser His Tyr Lys Ile
  1               5
```

(2) INFORMATION FOR SEQ ID NO: 20:

(i) SEQUENCE CHARACTERISTICS:
        (A) LENGTH: 77 base pairs
        (B) TYPE: nucleic acid
        (C) STRANDEDNESS: double
        (D) TOPOLOGY: circular (ii) MOLECULE TYPE: other nucleic acid (ix) FEATURE:

(A) NAME/KEY: CDS
        (B) LOCATION: 9..77

(xi) SEQUENCE DESCRIPTION: SEQ ID NO: 20:

GTTCCGTG CCG AAC CGC AGC CGC AGC AAG CTC TCG ACA GCC ATG AGC GCG         50
         Pro Asn Arg Ser Arg Ser Lys Leu Ser Thr Ala Met Ser Ala
                  10                  15

GTC GCC GCC CTG GCA GTT GCA AGT CCT                                      77
Val Ala Ala Leu Ala Val Ala Ser Pro
 20              25

(2) INFORMATION FOR SEQ ID NO: 21:

(i) SEQUENCE CHARACTERISTICS:
        (A) LENGTH: 23 amino acids
        (B) TYPE: amino acid
        (D) TOPOLOGY: linear (ii) MOLECULE TYPE: protein (xi) SEQUENCE DESCRIPTION: SEQ ID NO: 21:

Pro Asn Arg Ser Arg Ser Lys Leu Ser Thr Ala Met Ser Ala Val Ala
 1               5                  10                  15

Ala Leu Ala Val Ala Ser Pro
             20

(2) INFORMATION FOR SEQ ID NO: 22:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(ix) FEATURE:
        (A) NAME/KEY: CDS
        (B) LOCATION: 4..72

(xi) SEQUENCE DESCRIPTION: SEQ ID NO: 22:

GTG CCG AAC CGA CGC CGA TGC AAG CTC TCT ACA GCC ATA AGC ACG GTC          48
    Pro Asn Arg Arg Arg Cys Lys Leu Ser Thr Ala Ile Ser Thr Val
     25                  30                  35

GCC ACC CTA GCA ATC GCC AGT CCA                                          72
Ala Thr Leu Ala Ile Ala Ser Pro
 40              45

(2) INFORMATION FOR SEQ ID NO: 23:

(i) SEQUENCE CHARACTERISTICS:
        (A) LENGTH: 23 amino acids
        (B) TYPE: amino acid
        (D) TOPOLOGY: linear (ii) MOLECULE TYPE: protein (xi) SEQUENCE DESCRIPTION: SEQ ID NO: 23:

Pro Asn Arg Arg Arg Cys Lys Leu Ser Thr Ala Ile Ser Thr Val Ala
 1               5                  10                  15

Thr Leu Ala Ile Ala Ser Pro
             20

(2) INFORMATION FOR SEQ ID NO: 24:

(i) SEQUENCE CHARACTERISTICS:

(A) LENGTH: 24 base pairs
        (B) TYPE: nucleic acid
        (C) STRANDEDNESS: double
        (D) TOPOLOGY: circular (ii) MOLECULE TYPE: other nucleic acid (ix) FEATURE:
        (A) NAME/KEY: CDS
        (B) LOCATION: 1..12

(xi) SEQUENCE DESCRIPTION: SEQ ID NO: 24:

```
CAG TTC GGG ATC CGGATACGTA CG                                  24
Gln Phe Gly Ile
    25
```

(2) INFORMATION FOR SEQ ID NO: 25:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO: 25:

```
Gln Phe Gly Ile
  1
```

(2) INFORMATION FOR SEQ ID NO: 26:

(i) SEQUENCE CHARACTERISTICS:
        (A) LENGTH: 96 base pairs
        (B) TYPE: nucleic acid
        (C) STRANDEDNESS: double
        (D) TOPOLOGY: circular (ii) MOLECULE TYPE: other nucleic acid (ix) FEATURE:
        (A) NAME/KEY: CDS
        (B) LOCATION: 16..84

(xi) SEQUENCE DESCRIPTION: SEQ ID NO: 26:

```
GTCGAGGAGC CACCG ATG AAC CGG ATC GTC GCG CCC GCC GCC GCA AGC GTG     51
              Met Asn Arg Ile Val Ala Pro Ala Ala Ala Ser Val
                1               5                  10              15

GTG GTT GGT CTG TTG CTG GCG CCG GCC GCG ATC CGGATACGTA CG           96
Val Val Gly Leu Leu Leu Ala Pro Ala Ala Ile
            20                  25
```

(2) INFORMATION FOR SEQ ID NO: 27:

(i) SEQUENCE CHARACTERISTICS:
        (A) LENGTH: 23 amino acids
        (B) TYPE: amino acid
        (D) TOPOLOGY: linear (ii) MOLECULE TYPE: protein (xi) SEQUENCE DESCRIPTION: SEQ ID NO: 27:

```
Met Asn Arg Ile Val Ala Pro Ala Ala Ala Ser Val Val Val Gly Leu
  1               5                  10                  15

Leu Leu Ala Pro Ala Ala Ile
                20
```

(2) INFORMATION FOR SEQ ID NO: 28:

(i) SEQUENCE CHARACTERISTICS:

(A) LENGTH: 27 base pairs
        (B) TYPE: nucleic acid
        (C) STRANDEDNESS: double
        (D) TOPOLOGY: circular (ii) MOLECULE TYPE: other nucleic acid (ix) FEATURE:
        (A) NAME/KEY: CDS
        (B) LOCATION: 1..27

(xi) SEQUENCE DESCRIPTION: SEQ ID NO: 28:

```
TGG ACC GCC GAG GAG AAT CGG CAC GGC                          27
Trp Thr Ala Glu Glu Asn Arg His Gly
     25              30
```

(2) INFORMATION FOR SEQ ID NO: 29:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO: 29:

```
Trp Thr Ala Glu Glu Asn Arg His Gly
  1               5
```

(2) INFORMATION FOR SEQ ID NO: 30:

(i) SEQUENCE CHARACTERISTICS:
        (A) LENGTH: 27 base pairs
        (B) TYPE: nucleic acid
        (C) STRANDEDNESS: double
        (D) TOPOLOGY: circular (ii) MOLECULE TYPE: other nucleic acid (ix) FEATURE:
        (A) NAME/KEY: CDS
        (B) LOCATION: 1..27

(xi) SEQUENCE DESCRIPTION: SEQ ID NO: 30:

```
TGG ACT GCG GAA GAG AAT AGA CAT GGT                          27
Trp Thr Ala Glu Glu Asn Arg His Gly
 10              15
```

(2) INFORMATION FOR SEQ ID NO: 31:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO: 31:

```
Trp Thr Ala Glu Glu Asn Arg His Gly
  1               5
```

(2) INFORMATION FOR SEQ ID NO: 32:

(i) SEQUENCE CHARACTERISTICS:
        (A) LENGTH: 42 base pairs
        (B) TYPE: nucleic acid
        (C) STRANDEDNESS: double
        (D) TOPOLOGY: circular (ii) MOLECULE TYPE: other nucleic acid (ix) FEATURE:
            (A) NAME/KEY: CDS
            (B) LOCATION: 1..42

(xi) SEQUENCE DESCRIPTION: SEQ ID NO: 32:

```
AGT TTC CAG GAA CTG GCA ACC CGG ATT TCG CAC CGC AAT ACC        42
Ser Phe Gln Glu Leu Ala Thr Arg Ile Ser His Arg Asn Thr
 10              15                  20
```

(2) INFORMATION FOR SEQ ID NO: 33:

(i) SEQUENCE CHARACTERISTICS:
            (A) LENGTH: 14 amino acids
            (B) TYPE: amino acid
            (D) TOPOLOGY: linear (ii) MOLECULE TYPE: protein (xi) SEQUENCE DESCRIPTION: SEQ ID NO: 33:

```
Ser Phe Gln Glu Leu Ala Thr Arg Ile Ser His Arg Asn Thr
 1               5                  10
```

(2) INFORMATION FOR SEQ ID NO: 34:

(i) SEQUENCE CHARACTERISTICS:
            (A) LENGTH: 42 base pairs
            (B) TYPE: nucleic acid
            (C) STRANDEDNESS: double
            (D) TOPOLOGY: circular (ii) MOLECULE TYPE: other nucleic acid (ix) FEATURE:
            (A) NAME/KEY: CDS
            (B) LOCATION: 1..42

(xi) SEQUENCE DESCRIPTION: SEQ ID NO: 34:

```
TCA TTC CAG GAA AGG GCA ACC TTC ATT TCT CAT GGG AAC ACC        42
Ser Phe Gln Glu Arg Ala Thr Phe Ile Ser His Gly Asn Thr
 15                  20                  25
```

(2) INFORMATION FOR SEQ ID NO: 35:

(i) SEQUENCE CHARACTERISTICS:
            (A) LENGTH: 14 amino acids
            (B) TYPE: amino acid
            (D) TOPOLOGY: linear (ii) MOLECULE TYPE: protein (xi) SEQUENCE DESCRIPTION: SEQ ID NO: 35:

```
Ser Phe Gln Glu Arg Ala Thr Phe Ile Ser His Gly Asn Thr
 1               5                  10
```

(2) INFORMATION FOR SEQ ID NO: 36:

(i) SEQUENCE CHARACTERISTICS:
            (A) LENGTH: 426 base pairs
            (B) TYPE: nucleic acid
            (C) STRANDEDNESS: double
            (D) TOPOLOGY: linear (ii) MOLECULE TYPE: other nucleic acid (xi) SEQUENCE DESCRIPTION: SEQ ID NO: 36:

```
CGGCTTCGGA ATAGGCATTG CCCCCGATGT GCGGGCGCCG CTCGAGGACG AGCACGCGCT     60

TGTCGAGTTG GGTGGACACG CGCTCGGCAA TCGTCAGGCC GAAGAATCCT GAGCCGACG     120

CGAAAAGGTC AAAACGAGCG GTCATCGGTT GCATAGGGTA ACCGACCTTG CTGGCAAAA     180
```

```
CCGATTTGGC AGCTCGTGGC GGTCATGGCC CGAACGGGTT TCACCGCAGG TGCGCATGG      240

CGACCAGTGT GGTTGGCCGG AGGTCGTTTG GTCGCGATTG CCTCACGATT CGATATAAC     300

ACTCTAGTCA CATCAACCAC ACTCGTACCA TCGAGCGTGT GGGTTCATGC CATGCACTC     360

CGACCGCGGG AGCCGGCGAA CCCGGCGCCA CACATAATCC AGATTGAGGA GACTTCCGT     420

CCGAAC                                                                426
```

(2) INFORMATION FOR SEQ ID NO: 37:

(i) SEQUENCE CHARACTERISTICS:
        (A) LENGTH: 275 base pairs
        (B) TYPE: nucleic acid
        (C) STRANDEDNESS: double
        (D) TOPOLOGY: circular (ii) MOLECULE TYPE: other nucleic acid (xi) SEQUENCE DESCRIPTION: SEQ ID NO: 37:

```
GTCGCCTAAG CCCCGGGTCG GCCGAAAACG CACCCGCGGC CAAGGCGTCG GTCATTGCTT      60

CGGCCCGTGC ACAATTATTC GCCTAAGGGT CGCTAGGTGT TCTCGAGAGT TTTATCGCA     120

CGATTCCGTG TCGTCTCATT AATACCAATA GAAAACACAC GTAACATCAG CTGGTGCCG     180

CCCGCACCCG CGCGCCGACG ACGCTGCTCA CCGCGATGGC AGCGACCGTC GTCATCGTC     240

CGTGGATAGC GAATCGTCCA CCCGCCAGCT CCCAT                                275
```

(2) INFORMATION FOR SEQ ID NO: 38:

(i) SEQUENCE CHARACTERISTICS:
        (A) LENGTH: 855 base pairs
        (B) TYPE: nucleic acid
        (C) STRANDEDNESS: double
        (D) TOPOLOGY: linear (ii) MOLECULE TYPE: other nucleic acid (ix) FEATURE:
        (A) NAME/KEY: CDS
        (B) LOCATION: 1..852

(xi) SEQUENCE DESCRIPTION: SEQ ID NO: 38:

```
GTG CCG AAC CGC AGC CGC AGC AAG CTC TCG ACA GCC ATG AGC GCG GTC       48
Val Pro Asn Arg Ser Arg Ser Lys Leu Ser Thr Ala Met Ser Ala Val
 15                  20                  25                  30

GCC GCC CTG GCA GTT GCA AGT CCT TGT GCA TAT TTT CTT GTC TAC GAA       96
Ala Ala Leu Ala Val Ala Ser Pro Cys Ala Tyr Phe Leu Val Tyr Glu
                 35                  40                  45

TCA ACC GAA ACG ACC GAG CGG CCC GAG CAC CAT GAA TTC AAG CAG GCG      144
Ser Thr Glu Thr Thr Glu Arg Pro Glu His His Glu Phe Lys Gln Ala
             50                  55                  60

GCG GTG TTG ACC GAC CTG CCC GGC GAG CTG ATG TCC GCG CTA TCG CAG      192
Ala Val Leu Thr Asp Leu Pro Gly Glu Leu Met Ser Ala Leu Ser Gln
         65                  70                  75

GGG TTG TCC CAG TTC GGG ATC AAC ATA CCG CCG GTG CCC AGC CTG ACC      240
Gly Leu Ser Gln Phe Gly Ile Asn Ile Pro Pro Val Pro Ser Leu Thr
     80                  85                  90

GGG AGC GGC GAT GCC AGC ACG GGT CTA ACC GGT CCT GGC CTG ACT AGT      288
Gly Ser Gly Asp Ala Ser Thr Gly Leu Thr Gly Pro Gly Leu Thr Ser
 95                 100                 105                 110

CCG GGA TTG ACC AGC CCG GGA TTG ACC AGC CCG GGC CTC ACC GAC CCT      336
Pro Gly Leu Thr Ser Pro Gly Leu Thr Ser Pro Gly Leu Thr Asp Pro
                115                 120                 125
```

```
GCC CTT ACC AGT CCG GGC CTG ACG CCA ACC CTG CCC GGA TCA CTC GCC      384
Ala Leu Thr Ser Pro Gly Leu Thr Pro Thr Leu Pro Gly Ser Leu Ala
        130                 135                 140

GCG CCC GGC ACC ACC CTG GCG CCA ACG CCC GGC GTG GGG GCC AAT CCG      432
Ala Pro Gly Thr Thr Leu Ala Pro Thr Pro Gly Val Gly Ala Asn Pro
145                 150                 155

GCG CTC ACC AAC CCC GCG CTG ACC AGC CCG ACC GGG GCG ACG CCG GGA      480
Ala Leu Thr Asn Pro Ala Leu Thr Ser Pro Thr Gly Ala Thr Pro Gly
160                 165                 170

TTG ACC AGC CCG ACG GGT TTG GAT CCC GCG CTG GGC GGC GCC AAC GAA      528
Leu Thr Ser Pro Thr Gly Leu Asp Pro Ala Leu Gly Gly Ala Asn Glu
175                 180                 185                 190

ATC CCG ATT ACG ACG CCG GTC GGA TTG GAT CCC GGG GCT GAC GGC ACC      576
Ile Pro Ile Thr Thr Pro Val Gly Leu Asp Pro Gly Ala Asp Gly Thr
                195                 200                 205

TAT CCG ATC CTC GGT GAT CCA ACA CTG GGG ACC ATA CCG AGC AGC CCC      624
Tyr Pro Ile Leu Gly Asp Pro Thr Leu Gly Thr Ile Pro Ser Ser Pro
        210                 215                 220

GCC ACC ACC TCC ACC GGC GGC GGC GGT CTC GTC AAC GAC GTG ATG CAG      672
Ala Thr Thr Ser Thr Gly Gly Gly Gly Leu Val Asn Asp Val Met Gln
        225                 230                 235

GTG GCC AAC GAG TTG GGC GCC AGT CAG GCT ATC GAC CTG CTA AAA GGT      720
Val Ala Asn Glu Leu Gly Ala Ser Gln Ala Ile Asp Leu Leu Lys Gly
240                 245                 250

GTG CTA ATG CCG TCG ATC ATG CAG GCC GTC CAG AAT GGC GGC GCG GTC      768
Val Leu Met Pro Ser Ile Met Gln Ala Val Gln Asn Gly Gly Ala Val
255                 260                 265                 270

GCG CCG GCA GCC AGC CCG CCG GTC CCG CCC ATC CCC GCG GCC GCG GCG      816
Ala Pro Ala Ala Ser Pro Pro Val Pro Pro Ile Pro Ala Ala Ala Ala
                275                 280                 285

GTG CCA CCG ACG GAC CCA ATC ACC GTG CCG GTC GCC TAA                  855
Val Pro Pro Thr Asp Pro Ile Thr Val Pro Val Ala
        290                 295

(2) INFORMATION FOR SEQ ID NO: 39:

(i) SEQUENCE CHARACTERISTICS:
        (A) LENGTH: 284 amino acids
        (B) TYPE: amino acid
        (D) TOPOLOGY: linear (ii) MOLECULE TYPE: protein (xi) SEQUENCE DESCRIPTION: SEQ ID NO: 39:

Val Pro Asn Arg Ser Arg Ser Lys Leu Ser Thr Ala Met Ser Ala Val
 1               5                  10                  15

Ala Ala Leu Ala Val Ala Ser Pro Cys Ala Tyr Phe Leu Val Tyr Glu
                20                  25                  30

Ser Thr Glu Thr Thr Glu Arg Pro Glu His His Glu Phe Lys Gln Ala
            35                  40                  45

Ala Val Leu Thr Asp Leu Pro Gly Glu Leu Met Ser Ala Leu Ser Gln
        50                  55                  60

Gly Leu Ser Gln Phe Gly Ile Asn Ile Pro Pro Val Pro Ser Leu Thr
65                  70                  75                  80

Gly Ser Gly Asp Ala Ser Thr Gly Leu Thr Gly Pro Gly Leu Thr Ser
                85                  90                  95

Pro Gly Leu Thr Ser Pro Gly Leu Thr Ser Pro Gly Leu Thr Asp Pro
            100                 105                 110

Ala Leu Thr Ser Pro Gly Leu Thr Pro Thr Leu Pro Gly Ser Leu Ala
        115                 120                 125
```

```
Ala Pro Gly Thr Thr Leu Ala Pro Thr Pro Gly Val Gly Ala Asn Pro
    130                 135                 140

Ala Leu Thr Asn Pro Ala Leu Thr Ser Pro Thr Gly Ala Thr Pro Gly
145                 150                 155                 160

Leu Thr Ser Pro Thr Gly Leu Asp Pro Ala Leu Gly Gly Ala Asn Glu
                165                 170                 175

Ile Pro Ile Thr Thr Pro Val Gly Leu Asp Pro Gly Ala Asp Gly Thr
            180                 185                 190

Tyr Pro Ile Leu Gly Asp Pro Thr Leu Gly Thr Ile Pro Ser Ser Pro
        195                 200                 205

Ala Thr Thr Ser Thr Gly Gly Gly Leu Val Asn Asp Val Met Gln
    210                 215                 220

Val Ala Asn Glu Leu Gly Ala Ser Gln Ala Ile Asp Leu Leu Lys Gly
225                 230                 235                 240

Val Leu Met Pro Ser Ile Met Gln Ala Val Gln Asn Gly Gly Ala Val
                245                 250                 255

Ala Pro Ala Ala Ser Pro Pro Val Pro Pro Ile Pro Ala Ala Ala Ala
                260                 265                 270

Val Pro Pro Thr Asp Pro Ile Thr Val Pro Val Ala
                275                 280
```

(2) INFORMATION FOR SEQ ID NO: 40:

(i) SEQUENCE CHARACTERISTICS:
        (A) LENGTH: 855 base pairs
        (B) TYPE: nucleic acid
        (C) STRANDEDNESS: double
        (D) TOPOLOGY: linear (ii) MOLECULE TYPE: other nucleic acid (ix) FEATURE:
        (A) NAME/KEY: CDS
        (B) LOCATION: 1..852

(xi) SEQUENCE DESCRIPTION: SEQ ID NO: 40:

```
GTG CCG AAC CGA CGC CGA CGC AAG CTC TCG ACA GCC ATG AGC GCG GTC       48
Val Pro Asn Arg Arg Arg Arg Lys Leu Ser Thr Ala Met Ser Ala Val
285                 290                 295                 300

GCC GCC CTG GCA GTT GCA AGT CCT TGT GCA TAT TTT CTT GTC TAC GAA       96
Ala Ala Leu Ala Val Ala Ser Pro Cys Ala Tyr Phe Leu Val Tyr Glu
                305                 310                 315

TCA ACC GAA ACG ACC GAG CGG CCC GAG CAC CAT GAA TTC AAG CAG GCG      144
Ser Thr Glu Thr Thr Glu Arg Pro Glu His His Glu Phe Lys Gln Ala
                320                 325                 330

GCG GTG TTG ACC GAC CTG CCC GGC GAG CTG ATG TCC GCG CTA TCG CAG      192
Ala Val Leu Thr Asp Leu Pro Gly Glu Leu Met Ser Ala Leu Ser Gln
            335                 340                 345

GGG TTG TCC CAG TTC GGG ATC AAC ATA CCG CCG GTG CCC AGC CTG ACC      240
Gly Leu Ser Gln Phe Gly Ile Asn Ile Pro Pro Val Pro Ser Leu Thr
        350                 355                 360

GGG AGC GGC GAT GCC AGC ACG GGT CTA ACC GGT CCT GGC CTG ACT AGT      288
Gly Ser Gly Asp Ala Ser Thr Gly Leu Thr Gly Pro Gly Leu Thr Ser
365                 370                 375                 380

CCG GGA TTG ACC AGC CCG GGA TTG ACC AGC CCG GGC CTC ACC GAC CCT      336
Pro Gly Leu Thr Ser Pro Gly Leu Thr Ser Pro Gly Leu Thr Asp Pro
                385                 390                 395

GCC CTT ACC AGT CCG GGC CTG ACG CCA ACC CTG CCC GGA TCA CTC GCC      384
Ala Leu Thr Ser Pro Gly Leu Thr Pro Thr Leu Pro Gly Ser Leu Ala
                400                 405                 410
```

```
GCG CCC GGC ACC ACC CTG GCG CCA ACG CCC GGC GTG GGG GCC AAT CCG      432
Ala Pro Gly Thr Thr Leu Ala Pro Thr Pro Gly Val Gly Ala Asn Pro
            415                 420                 425

GCG CTC ACC AAC CCC GCG CTG ACC AGC CCG ACC GGG GCG ACG CCG GGA      480
Ala Leu Thr Asn Pro Ala Leu Thr Ser Pro Thr Gly Ala Thr Pro Gly
        430                 435                 440

TTG ACC AGC CCG ACG GGT TTG GAT CCC GCG CTG GGC GGC GCC AAC GAA      528
Leu Thr Ser Pro Thr Gly Leu Asp Pro Ala Leu Gly Gly Ala Asn Glu
445                 450                 455                 460

ATC CCG ATT ACG ACG CCG GTC GGA TTG GAT CCC GGG GCT GAC GGC ACC      576
Ile Pro Ile Thr Thr Pro Val Gly Leu Asp Pro Gly Ala Asp Gly Thr
            465                 470                 475

TAT CCG ATC CTC GGT GAT CCA ACA CTG GGG ACC ATA CCG AGC AGC CCC      624
Tyr Pro Ile Leu Gly Asp Pro Thr Leu Gly Thr Ile Pro Ser Ser Pro
        480                 485                 490

GCC ACC ACC TCC ACC GGC GGC GGT CTC GTC AAC GAC GTG ATG CAG          672
Ala Thr Thr Ser Thr Gly Gly Gly Leu Val Asn Asp Val Met Gln
                495                 500                 505

GTG GCC AAC GAG TTG GGC GCC AGT CAG GCT ATC GAC CTG CTA AAA GGT      720
Val Ala Asn Glu Leu Gly Ala Ser Gln Ala Ile Asp Leu Leu Lys Gly
510                 515                 520

GTG CTA ATG CCG TCG ATC ATG CAG GCC GTC CAG AAT GGC GGC GCG GTC      768
Val Leu Met Pro Ser Ile Met Gln Ala Val Gln Asn Gly Gly Ala Val
525                 530                 535                 540

GCG CCG GCA GCC AGC CCG CCG GTC CCG CCC ATC CCC GCG GCC GCG GCG      816
Ala Pro Ala Ala Ser Pro Pro Val Pro Pro Ile Pro Ala Ala Ala Ala
            545                 550                 555

GTG CCA CCG ACG GAC CCA ATC ACC GTG CCG GTC GCC TAA                  855
Val Pro Pro Thr Asp Pro Ile Thr Val Pro Val Ala
                560                 565

(2) INFORMATION FOR SEQ ID NO: 41:

(i) SEQUENCE CHARACTERISTICS:
        (A) LENGTH: 284 amino acids
        (B) TYPE: amino acid
        (D) TOPOLOGY: linear (ii) MOLECULE TYPE: protein (xi) SEQUENCE DESCRIPTION: SEQ ID NO: 41:

Val Pro Asn Arg Arg Arg Lys Leu Ser Thr Ala Met Ser Ala Val
 1               5                  10                  15

Ala Ala Leu Ala Val Ala Ser Pro Cys Ala Tyr Phe Leu Val Tyr Glu
                20                  25                  30

Ser Thr Glu Thr Thr Glu Arg Pro Glu His His Glu Phe Lys Gln Ala
            35                  40                  45

Ala Val Leu Thr Asp Leu Pro Gly Glu Leu Met Ser Ala Leu Ser Gln
        50                  55                  60

Gly Leu Ser Gln Phe Gly Ile Asn Ile Pro Pro Val Pro Ser Leu Thr
65                  70                  75                  80

Gly Ser Gly Asp Ala Ser Thr Gly Leu Thr Gly Pro Gly Leu Thr Ser
                85                  90                  95

Pro Gly Leu Thr Ser Pro Gly Leu Thr Ser Pro Gly Leu Thr Asp Pro
            100                 105                 110

Ala Leu Thr Ser Pro Gly Leu Thr Pro Thr Leu Pro Gly Ser Leu Ala
        115                 120                 125

Ala Pro Gly Thr Thr Leu Ala Pro Thr Pro Gly Val Gly Ala Asn Pro
    130                 135                 140
```

```
Ala Leu Thr Asn Pro Ala Leu Thr Ser Pro Thr Gly Ala Thr Pro Gly
145                 150                 155                 160

Leu Thr Ser Pro Thr Gly Leu Asp Pro Ala Leu Gly Gly Ala Asn Glu
            165                 170                 175

Ile Pro Ile Thr Thr Pro Val Gly Leu Asp Pro Gly Ala Asp Gly Thr
            180                 185                 190

Tyr Pro Ile Leu Gly Asp Pro Thr Leu Gly Thr Ile Pro Ser Ser Pro
            195                 200                 205

Ala Thr Thr Ser Thr Gly Gly Gly Leu Val Asn Asp Val Met Gln
210                 215                 220

Val Ala Asn Glu Leu Gly Ala Ser Gln Ala Ile Asp Leu Leu Lys Gly
225                 230                 235                 240

Val Leu Met Pro Ser Ile Met Gln Ala Val Gln Asn Gly Gly Ala Val
            245                 250                 255

Ala Pro Ala Ala Ser Pro Pro Val Pro Pro Ile Pro Ala Ala Ala Ala
            260                 265                 270

Val Pro Pro Thr Asp Pro Ile Thr Val Pro Val Ala
            275                 280
```

(2) INFORMATION FOR SEQ ID NO: 42:

(i) SEQUENCE CHARACTERISTICS:
        (A) LENGTH: 34 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO: 42:

CATTTCTCAT TGATAATGAG AATCATTATT GACA                        34

(2) INFORMATION FOR SEQ ID NO: 43:

(i) SEQUENCE CHARACTERISTICS:
        (A) LENGTH: 34 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO: 43:

AGCCTCTCTT TGAATATGAT TATCATTTTC ATTA                        34

(2) INFORMATION FOR SEQ ID NO: 44:

(i) SEQUENCE CHARACTERISTICS:
        (A) LENGTH: 34 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO: 44:

TATTATCTTA TCTTTATAAT AATCATTCTC GTTT                        34

(2) INFORMATION FOR SEQ ID NO: 45:

(i) SEQUENCE CHARACTERISTICS:
        (A) LENGTH: 34 base pairs
        (B) TYPE: nucleic acid (C) STRANDEDNESS: double
        (D) TOPOLOGY: linear (ii) MOLECULE TYPE: other nucleic acid (xi) SEQUENCE DESCRIPTION: SEQ ID NO: 45:

TATATTAGTA ATATTATGAT AACTATTTGC ATTT                                34

(2) INFORMATION FOR SEQ ID NO: 46:

(i) SEQUENCE CHARACTERISTICS:
        (A) LENGTH: 34 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO: 46:

CGTGGCAATT CTATAATGAT ACGCATTATC TCAA                                34

(2) INFORMATION FOR SEQ ID NO: 47:

(i) SEQUENCE CHARACTERISTICS:
        (A) LENGTH: 34 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO: 47:

TGAATGCGTA TATTTCTCAT TTGCATTTAC AAAC                                34

(2) INFORMATION FOR SEQ ID NO: 48:

(i) SEQUENCE CHARACTERISTICS:
        (A) LENGTH: 34 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO: 48:

TTATTGAATA TGATTGCTAT TTGCATTTAA ATCG                                34

(2) INFORMATION FOR SEQ ID NO: 49:

(i) SEQUENCE CHARACTERISTICS:
        (A) LENGTH: 34 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO: 49:

TAATTAGGAT AGCTTTACCT AATTATTTTA TAGC                                34

(2) INFORMATION FOR SEQ ID NO: 50:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO: 50:

GATAATGATA ATCATTATC                                                        19

(2) INFORMATION FOR SEQ ID NO: 51:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO: 51:

CAATTACCTC ACGATTCAAT ATAACCACTC TGGTCA                                      36

(2) INFORMATION FOR SEQ ID NO: 52:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO: 52:

GATTCAATAT AACCACTCTG                                                        20

(2) INFORMATION FOR SEQ ID NO: 53:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO: 53:

GATTCGATAT AACCACTCTA                                                        20

(2) INFORMATION FOR SEQ ID NO: 54:

(i) SEQUENCE CHARACTERISTICS:
        (A) LENGTH: 847 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO: 54:

GTGCCGAACC GCAGCCGCAG CAAGCTCTCG ACAGCCATGA GCGCGGTCGC CGCCCTGGCA           60

GTTGCAAGTC CTTGTGCATA TTTTCTTGTC TACGAATCAA CCGAAACGAC CGAGCGGCC           120

GAGCACCATG AATTCAAGCA GGCGGCGGTG TTGACCGACC TGCCCGGCGA GCTGATGTC           180

GCGCTATCGC AGGGGTTGTC CCAGTTCGGG ATCAACATAC CGCCGGTGCC CAGCCTGAC           240

GGGAGCGGCG ATGCCAGCAC GGGTCTAACC GGTCCTGGCC TGACTAGTCC GGGATTGAC           300

AGCCCGGGAT TGACCAGCCC GGGCCTCACC GACCCTGCCC TTACCAGTCC GGGCCTGAC           360

CCAACCCTGC CCGGATCACT CGCCGCGCCC GGCACCACCC TGGCGCCAAC GCCCGGCGT           420

GGGGCCAATC CGGCGCTCAC CAACCCCGCG CTGACCAGCC CGACCGGGGC GACGCCGGG           480

-continued

```
TTGACCAGCC CGACGGGTTT GGATCCCGCG CTGGGCGGCG CCAACGAAAT CCCGATTAC      540

ACGCCGGTCG GATTGGATCC CGGGGCTGAC GGCACCTATC CGATCCTCGG TGATCCAAC      600

CTGGGGACCA TACCGAGCAG CCCCGCCACC ACCTCCACCG GCGGCGGCGG TCTCGTCAA      660

GACGTGATGC AGGTGGCCAA CGAGTTGGGC GCCAGTCAGG CTATCGACCT GCTAAAAGG      720

GTGCTAATGC CGTCGATCAT GCAGGCCGTC CAGAATGGCG GCGCGGTCGC GCCGGCAGC      780

AGCCCGCCGG TCCCGCCCAT CCCCGCGCC GCGGCGGTGC CACCGACGGA CCCAATCAC       840

GTGCCGG                                                               847
```

(2) INFORMATION FOR SEQ ID NO: 55:

(i) SEQUENCE CHARACTERISTICS:
        (A) LENGTH: 711 base pairs
        (B) TYPE: nucleic acid
        (C) STRANDEDNESS: double
        (D) TOPOLOGY: linear (ii) MOLECULE TYPE: other nucleic acid (ix) FEATURE:
        (A) NAME/KEY: CDS
        (B) LOCATION: 1..708

(xi) SEQUENCE DESCRIPTION: SEQ ID NO: 55:

```
GTG CCG AAC CGA CGC CGA TGC AAG CTT TCG ACA GCC ATA AGC ACG GTC       48
Val Pro Asn Arg Arg Arg Cys Lys Leu Ser Thr Ala Ile Ser Thr Val
285             290                 295                 300

GCC ACC CTA GCA ATC GCC AGT CCA TGC GCA TAT TTC CTT GTT TAC GAA       96
Ala Thr Leu Ala Ile Ala Ser Pro Cys Ala Tyr Phe Leu Val Tyr Glu
                305                 310                 315

CCG ACC GCG AGC GCC AAA CCC GCG GCC AAA CAC TAT GAA TTC AAA CAA      144
Pro Thr Ala Ser Ala Lys Pro Ala Ala Lys His Tyr Glu Phe Lys Gln
                    320                 325                 330

GCA GCA TCG ATA GCC GAC CTG CCC GGA GAA GTG CTG GAC GCG ATC TCG      192
Ala Ala Ser Ile Ala Asp Leu Pro Gly Glu Val Leu Asp Ala Ile Ser
                335                 340                 345

CAG GGA CTG TCG CAG TTC GGC ATC AAC CTA CCG CCG GTG CCT TCG CTA      240
Gln Gly Leu Ser Gln Phe Gly Ile Asn Leu Pro Pro Val Pro Ser Leu
350                 355                 360

ACT GGC ACC GAT GAT CCA GGT AAT GGC CTG AGA ACT CCC GGT TTG ACC      288
Thr Gly Thr Asp Asp Pro Gly Asn Gly Leu Arg Thr Pro Gly Leu Thr
365                 370                 375                 380

AGC CCC GAT CTG ACA AAT CAG GAG CTA GGG ACA CCT GTG CTC ACC GCG      336
Ser Pro Asp Leu Thr Asn Gln Glu Leu Gly Thr Pro Val Leu Thr Ala
                385                 390                 395

CCG GGC ACG GGA CTG ACA CCA CCT GTG ACA GGC AGC CCG ATA TGT ACC      384
Pro Gly Thr Gly Leu Thr Pro Pro Val Thr Gly Ser Pro Ile Cys Thr
                    400                 405                 410

GCA CCG GAC CTG AAC CTG GGT GGC ACC TGC CCC AGC GAG GTA CCG ATC      432
Ala Pro Asp Leu Asn Leu Gly Gly Thr Cys Pro Ser Glu Val Pro Ile
                415                 420                 425

ACC ACA CCA ATT TCA TTG GAC CCG GGC ACC GAC GGC ACC TAT CCG ATC      480
Thr Thr Pro Ile Ser Leu Asp Pro Gly Thr Asp Gly Thr Tyr Pro Ile
430                 435                 440

CTC GGC GAT CCC TCC ACG TTG GGC GGT ACA TCA CCG ATC AGT ACC AGC      528
Leu Gly Asp Pro Ser Thr Leu Gly Gly Thr Ser Pro Ile Ser Thr Ser
445                 450                 455                 460

AGC GGT GAG CTT GTA AAT GAC CTG CTA AAA GTT GCG AAC CAG TTG GGC      576
Ser Gly Glu Leu Val Asn Asp Leu Leu Lys Val Ala Asn Gln Leu Gly
                465                 470                 475
```

-continued

```
GCC AGC CAG GTC ATG GAC CTA ATC AAG GGT GTG GTG ATG CCA GCG GTC      624
Ala Ser Gln Val Met Asp Leu Ile Lys Gly Val Val Met Pro Ala Val
            480                 485                 490

ATG CAG GGC GTC CAG AAC GGC AAC GTA GCC GGT GAC TTG TCG GGC TCA      672
Met Gln Gly Val Gln Asn Gly Asn Val Ala Gly Asp Leu Ser Gly Ser
            495                 500                 505

GTA ACG CCG GCC GCG ATA TCA CTG ATT CCT GTC ACG TAG                  711
Val Thr Pro Ala Ala Ile Ser Leu Ile Pro Val Thr
            510                 515                 520
```

(2) INFORMATION FOR SEQ ID NO: 56:

(i) SEQUENCE CHARACTERISTICS:
        (A) LENGTH: 236 amino acids
        (B) TYPE: amino acid
        (D) TOPOLOGY: linear (ii) MOLECULE TYPE: protein (xi) SEQUENCE DESCRIPTION: SEQ ID NO: 56:

```
Val Pro Asn Arg Arg Arg Cys Lys Leu Ser Thr Ala Ile Ser Thr Val
 1               5                  10                  15

Ala Thr Leu Ala Ile Ala Ser Pro Cys Ala Tyr Phe Leu Val Tyr Glu
            20                  25                  30

Pro Thr Ala Ser Ala Lys Pro Ala Ala Lys His Tyr Glu Phe Lys Gln
            35                  40                  45

Ala Ala Ser Ile Ala Asp Leu Pro Gly Glu Val Leu Asp Ala Ile Ser
            50                  55                  60

Gln Gly Leu Ser Gln Phe Gly Ile Asn Leu Pro Pro Val Pro Ser Leu
 65                  70                  75                  80

Thr Gly Thr Asp Asp Pro Gly Asn Gly Leu Arg Thr Pro Gly Leu Thr
            85                  90                  95

Ser Pro Asp Leu Thr Asn Gln Glu Leu Gly Thr Pro Val Leu Thr Ala
            100                 105                 110

Pro Gly Thr Gly Leu Thr Pro Pro Val Thr Gly Ser Pro Ile Cys Thr
            115                 120                 125

Ala Pro Asp Leu Asn Leu Gly Gly Thr Cys Pro Ser Glu Val Pro Ile
            130                 135                 140

Thr Thr Pro Ile Ser Leu Asp Pro Gly Thr Asp Gly Thr Tyr Pro Ile
145                 150                 155                 160

Leu Gly Asp Pro Ser Thr Leu Gly Gly Thr Ser Pro Ile Ser Thr Ser
            165                 170                 175

Ser Gly Glu Leu Val Asn Asp Leu Leu Lys Val Ala Asn Gln Leu Gly
            180                 185                 190

Ala Ser Gln Val Met Asp Leu Ile Lys Gly Val Val Met Pro Ala Val
            195                 200                 205

Met Gln Gly Val Gln Asn Gly Asn Val Ala Gly Asp Leu Ser Gly Ser
            210                 215                 220

Val Thr Pro Ala Ala Ile Ser Leu Ile Pro Val Thr
225                 230                 235
```

(2) INFORMATION FOR SEQ ID NO: 57:

(i) SEQUENCE CHARACTERISTICS:
        (A) LENGTH: 284 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 57:

Met Pro Asn Arg Arg Arg Arg Lys Leu Ser Thr Ala Met Ser Ala Va
1               5                   10                  15

Ala Ala Leu Ala Val Ala Ser Pro Cys Ala Tyr Phe Leu Val Tyr Gl
            20                  25                  30

Ser Thr Glu Thr Thr Glu Arg Pro Glu His His Glu Phe Lys Gln Al
            35                  40                  45

Ala Val Leu Thr Asp Leu Pro Gly Glu Leu Met Ser Ala Leu Ser Gl
        50                  55                  60

Gly Leu Ser Gln Phe Gly Ile Asn Ile Pro Pro Val Pro Ser Leu Th
65                  70                  75                  80

Gly Ser Gly Asp Ala Ser Thr Gly Leu Thr Gly Pro Gly Leu Thr Se
                85                  90                  95

Pro Gly Leu Thr Ser Pro Gly Leu Thr Ser Pro Gly Leu Thr Asp Pr
            100                 105                 110

Ala Leu Thr Ser Pro Gly Leu Thr Pro Thr Leu Pro Gly Ser Leu Al
            115                 120                 125

Ala Pro Gly Thr Thr Leu Ala Pro Thr Pro Gly Val Gly Ala Asn Pr
        130                 135                 140

Ala Leu Thr Asn Pro Ala Leu Thr Ser Pro Thr Gly Ala Thr Pro Gl
145                 150                 155                 160

Leu Thr Ser Pro Thr Gly Leu Asp Pro Ala Leu Gly Gly Ala Asn Gl
                165                 170                 175

Ile Pro Ile Thr Thr Pro Val Gly Leu Asp Pro Gly Ala Asp Gly Th
            180                 185                 190

Tyr Pro Ile Leu Gly Asp Pro Thr Leu Gly Thr Ile Pro Ser Ser Pr
            195                 200                 205

Ala Thr Thr Ser Thr Gly Gly Gly Gly Leu Val Asn Asp Val Met Gl
        210                 215                 220

Val Ala Asn Glu Leu Gly Ala Ser Gln Ala Ile Asp Leu Leu Lys Gl
225                 230                 235                 240

Val Leu Met Pro Ser Ile Met Gln Ala Val Gln Asn Gly Gly Ala Va
                245                 250                 255

Ala Pro Ala Ala Ser Pro Pro Val Pro Pro Ile Pro Ala Ala Ala Al
            260                 265                 270

Val Pro Pro Thr Asp Pro Ile Thr Val Pro Val Ala
            275                 280

(2) INFORMATION FOR SEQ ID NO: 58:

(i) SEQUENCE CHARACTERISTICS:
        (A) LENGTH: 236 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 58:

Met Pro Asn Arg Arg Arg Cys Lys Leu Ser Thr Ala Ile Ser Thr Va
1               5                   10                  15

Ala Thr Leu Ala Ile Ala Ser Pro Cys Ala Tyr Phe Leu Val Tyr Gl
            20                  25                  30

Pro Thr Ala Ser Ala Lys Pro Ala Ala Lys His Tyr Glu Phe Lys Gl
            35                  40                  45

```
Ala Ala Ser Ile Ala Asp Leu Pro Gly Glu Val Leu Asp Ala Ile Se
 50                  55                  60
Gln Gly Leu Ser Gln Phe Gly Ile Asn Leu Pro Pro Val Pro Ser Le
 65                  70                  75                  80
Thr Gly Thr Asp Asp Pro Gly Asn Gly Leu Arg Thr Pro Gly Leu Th
                 85                  90                  95
Ser Pro Asp Leu Thr Asn Gln Glu Leu Gly Thr Pro Val Leu Thr Al
                100                 105                 110
Pro Gly Thr Gly Leu Thr Pro Pro Val Thr Gly Ser Pro Ile Cys Th
                115                 120                 125
Ala Pro Asp Leu Asn Leu Gly Gly Thr Cys Pro Ser Glu Val Pro Il
130                 135                 140
Thr Thr Pro Ile Ser Leu Asp Pro Gly Thr Asp Gly Thr Tyr Pro Il
145                 150                 155                 160
Leu Gly Asp Pro Ser Thr Leu Gly Gly Thr Ser Pro Ile Ser Thr Se
                165                 170                 175
Ser Gly Glu Leu Val Asn Asp Leu Leu Lys Val Ala Asn Gln Leu Gl
                180                 185                 190
Ala Ser Gln Val Met Asp Leu Ile Lys Gly Val Val Met Pro Ala Va
                195                 200                 205
Met Gln Gly Val Gln Asn Gly Asn Val Ala Gly Asp Leu Ser Gly Se
    210                 215                 220
Val Thr Pro Ala Ala Ile Ser Leu Ile Pro Val Thr
225                 230                 235

(2) INFORMATION FOR SEQ ID NO: 59:

(i) SEQUENCE CHARACTERISTICS:
        (A) LENGTH: 212 base pairs
        (B) TYPE: nucleic acid
        (C) STRANDEDNESS: double
        (D) TOPOLOGY: circular (ii) MOLECULE TYPE: other nucleic acid (ix) FEATURE:
        (A) NAME/KEY: CDS
        (B) LOCATION: 159..207

(xi) SEQUENCE DESCRIPTION: SEQ ID NO: 59:

ATGACCTTTA ATAGATTATA TTACTAATTA ATTGGGGACC CTAGAGGTCC CCTTTTTAAA    60

AATTTTTTCA CAAAACGGTT TACAAGCATA AAGCTAGTAC TGGGCCCGCG GATCCGCAT    120

CGGTACCAAG CTTGATCCGA TAACACAGGA ACAGATCT ATG GTT CGT GCA AAC       173
                                          Met Val Arg Ala Asn
                                                              240

AAA CGC AAC GAG GCT CTA CGA ATC GGA AGC TTC  G ATCCC                 212
Lys Arg Asn Glu Ala Leu Arg Ile Gly Ser Phe
        245                 250

(2) INFORMATION FOR SEQ ID NO: 60:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO: 60:

Met Val Arg Ala Asn Lys Arg Asn Glu Ala Leu Arg Ile Gly Ser Phe
 1               5                  10                  15
```

-continued (2) INFORMATION FOR SEQ ID NO: 61:

(i) SEQUENCE CHARACTERISTICS:
(A) LENGTH: 143 base pairs
(B) TYPE: nucleic acid
(C) STRANDEDNESS: double
(D) TOPOLOGY: circular (ii) MOLECULE TYPE: other nucleic acid (xi) SEQUENCE DESCRIPTION: SEQ ID NO: 61:

```
ATGACCTTTA ATAGATTATA TTACTAATTA ATTGGGGACC CTAGAGGTCC CCTTTTTAAA      60

AATTTTTTCA CAAAACGGTT TACAAGCATA AAGCTAGTAC TGGGCCCGCG GATCCGGAT      120

CGTACGGTAC CAAGCTTGCT CCC                                             143
```

(2) INFORMATION FOR SEQ ID NO: 62:

(i) SEQUENCE CHARACTERISTICS:
(A) LENGTH: 144 base pairs
(B) TYPE: nucleic acid
(C) STRANDEDNESS: double
(D) TOPOLOGY: circular (ii) MOLECULE TYPE: other nucleic acid (xi) SEQUENCE DESCRIPTION: SEQ ID NO: 62:

```
ATGACCTTTA ATAGATTATA TTACTAATTA ATTGGGGACC CTAGAGGTCC CCTTTTTAAA      60

AATTTTTTCA CAAAACGGTT TACAAGCATA AAGCTAGTAC TGGGCCCGCG GATCCGGAT      120

CGTACGGTAC CAAGCTTCGA TCCC                                            144
```

(2) INFORMATION FOR SEQ ID NO: 63:

(i) SEQUENCE CHARACTERISTICS:
(A) LENGTH: 145 base pairs
(B) TYPE: nucleic acid
(C) STRANDEDNESS: double
(D) TOPOLOGY: circular (ii) MOLECULE TYPE: other nucleic acid (xi) SEQUENCE DESCRIPTION: SEQ ID NO: 63:

```
ATGACCTTTA ATAGATTATA TTACTAATTA ATTGGGGACC CTAGAGGTCC CCTTTTTAAA      60

AATTTTTTCA CAAAACGGTT TACAAGCATA AAGCTAGTAC TGGGCCCGCG GATCCGGAT      120

CGTACGGTAC CAAGCTTGCG ATCCC                                           145
```